United States Patent
Lo et al.

(10) Patent No.: US 9,556,490 B2
(45) Date of Patent: Jan. 31, 2017

(54) METHODS FOR ASSESSING LIVER PATHOLOGIES

(71) Applicant: The Chinese University of Hong Kong, Shatin, New Territories (CN)

(72) Inventors: Yuk Ming Dennis Lo, Kowloon (CN); Rossa Wai Kwun Chiu, Shatin (CN); Rebecca Wing Yan Chan, Tai Po (CN)

(73) Assignee: The Chinese University of Hong Kong, Shatin, N.T., Hong Kong SAR (CN)

( * ) Notice: Subject to any disclaimer, the term of this patent is extended or adjusted under 35 U.S.C. 154(b) by 0 days.

(21) Appl. No.: 14/703,689

(22) Filed: May 4, 2015

(65) Prior Publication Data

US 2015/0284801 A1 Oct. 8, 2015

Related U.S. Application Data

(62) Division of application No. 12/879,600, filed on Sep. 10, 2010, now Pat. No. 9,051,614.

(60) Provisional application No. 61/241,709, filed on Sep. 11, 2009.

(51) Int. Cl.
*C12Q 1/68* (2006.01)

(52) U.S. Cl.
CPC ........ *C12Q 1/6883* (2013.01); *C12Q 2600/118* (2013.01); *C12Q 2600/156* (2013.01); *C12Q 2600/158* (2013.01); *Y10T 436/143333* (2015.01)

(58) Field of Classification Search
None
See application file for complete search history.

(56) References Cited

FOREIGN PATENT DOCUMENTS

| JP | 2007-252366 A | 10/2007 |
|---|---|---|
| JP | 2009-095343 A | 5/2009 |

OTHER PUBLICATIONS

Chan, R., et al., "Aberrant Concentrations of Liver-Derived Plasma Albumin mRNA in Liver Pathologies," *Clinical Chemistry*, vol. 56(1), pp. 82-89 (Jan. 1, 2010).
Cheung, S., et al., "Albumin mRNA in Plasma Predicts Post-Transplant Recurrence of Patients With Hepatocellular Carcinoma," *Transplantation*, vol. 85(1), pp. 81-87 (Jan. 15, 2008).
Kudo, Y., et al., "Utility of Plasma Circulating mRNA as a Marker to Detect Hepatic Injury," *J. Vet. Med. Sci.*, vol. 70(9), pp. 993-995 (Sep. 2008).
Lok et al, "Chronic Hepatitis B," *Hepatology*, vol. 45, No. 2; pp. 507-539 (Feb. 2007).
Miyamoto, M., et al., "Detection of Cell-Free, Liver-Specific mRNAs in Peripheral Blood from Rats with Hepatotoxicity: A Potential Toxicological Biomarker for Safety Evaluation," *Toxicological Sciences*, vol. 106(2), pp. 538-545 (Dec. 2008).
Mofrad et al., "Clinical and Histologic Spectrum of Nonalcoholic Fatty Liver Disease Associated With Normal AL T Values," *Hepatology*, vol. 37, No. 6, pp. 1286-1292, published Dec. 30, 2003
Roberts et al., "A practice guideline on Wilson disease," *Hepatology*, vol. 37, No. 6; pp. 1475-1492 (Jun. 2003)
Roberts et al., "Diagnosis and treatment of Wilson disease: an update", *Hepatology*, vol. 47, p. 2089-2111 (2008).
Tsui et al., "Stability of endogenous and added RNA in blood specimens, serum and plasma," *Clinical Chemistry*, vol. 48, No. 10, pp. 1647-1653 (Oct. 2002).
Vogelstein et al., "Digital PCR," *Proc. Natl. Acad. Sci. USA*, vol. 96; pp. 9236-9241, (Aug. 1999).
Stratagene catalog; 1988; p. 39.
International Search Report and Written Opinion of the European International Searching Authority corresponding to PCT application No. PCT/EP2010/063300.

*Primary Examiner* — Antonio Galisteo Gonzalez
(74) *Attorney, Agent, or Firm* — Kilpatrick Townsend & Stockton LLP

(57) ABSTRACT

The present invention provides a new method for detecting or monitoring a liver disease in a subject that has no indication of any liver pathologies, by measuring the amount of concentration of albumin mRNA in an acellular blood sample from the subject, and then comparing the amount or concentration of albumin mRNA with a standard control.

14 Claims, 18 Drawing Sheets ively on the vital importance of early detection and
METHODS FOR ASSESSING LIVER PATHOLOGIES

RELATED APPLICATIONS

This application is a division of U.S. patent application Ser. No. 12/879,600, now U.S. Pat. No. 9,051,614, which claims priority to U.S. Patent No. 61/241,709, filed Sep. 11, 2009, the contents of each are incorporated by reference in the entirety.

REFERENCE TO SUBMISSION OF A SEQUENCE LISTING

This application includes a Sequence Listing as a text file named "80015-942245_SEQ" created Jun. 17, 2015 and containing 3,108 bytes. The material contained in this text file is incorporated by reference in its entirety for all purposes.

BACKGROUND OF THE INVENTION

Many potentially life-threatening liver diseases affect a significant portion of the human population. One such example is hepatitis B, a liver infection caused by the hepatitis B virus (HBV). It is a major global health problem and the most serious type of viral hepatitis, due to its potential of causing chronic liver diseases, which may ultimately lead to cirrhosis of the liver and liver cancer. Worldwide, an estimated two billion people have been infected with the HBV, and more than 350 million have chronic liver infections though many are asymptomatic. Hepatitis B is endemic in China and other parts of Asia. Most people in those regions become infected with HBV during childhood, and 8% to 10% of the adult population are chronically infected. Liver cancer caused by HBV is among the first three causes of death from cancer in men, and a major cause of cancer in women.

A number of liver function tests have been developed and routinely used in clinics. For example, a patient's blood sample may be tested for the level of alanine transaminase (ALT), aspartate transaminase (AST), alkaline phosphatase (ALP), total bilirubin (TBIL), direct bilirubin, or gamma glutamyl transpeptidase (GGT) for the purpose of assessing liver function. However, because of the high prevalence of liver diseases and the vital importance of early detection and treatment, especially in view of the fact that most liver diseases show only mild symptoms initially, there exists a need for new and more sensitive methods that would allow early diagnosis of liver diseases. This invention fulfills this and other related needs.

BRIEF SUMMARY OF THE INVENTION

In one aspect, the present invention provides a method for detecting a liver disease in a subject who has no indication of a liver disease, for example, the person never had abnormal alanine aminotransferase (ALT) test results. The method includes these steps: (a) determining the amount or concentration of albumin mRNA in an acellular blood sample taken from the subject; and (b) comparing the amount or concentration of albumin mRNA from step (a) with a standard control. An increase in the amount or concentration obtained from step (a) when compared to the standard control indicates the presence of a liver disease in the subject. Whereas the amount or concentration of albumin mRNA from step (a) is substantially the same as the standard control, the subject is then deemed to be free of a liver disease.

In some embodiments, the subject being tested is a person not at risk of developing a liver disease. Some examples of the liver diseases to be tested for include fatty liver disease such as nonalcoholic fatty liver disease, cirrhosis, liver fibrosis, or hepatitis (e.g., hepatitis A, B, or C). Other examples include Wilson disease, hemochromatosis, alpha 1-antitrypsin deficiency, or glycogen storage disease. In some embodiments, hepatocellular carcinoma, especially hepatocellular carcinoma occurred in a post-liver transplant patient, is excluded from the list of liver diseases being tested for using the method of this invention.

In some embodiment, the acellular blood sample is plasma. In other embodiments, the acellular blood sample is serum.

In some embodiments of the claimed method, step (a) comprises amplification of the albumin mRNA sequence, such as by a polymerase chain reaction (PCR), including reverse transcriptase (RT)-PCR, digital PCR, or real-time quantitative PCR. In other embodiments, step (a) comprises mass spectrometry or hybridization to a microarray, fluorescence probe, or molecular beacon.

In some cases, the claimed method may further involve repeating step (a) at a later time using the same type of acellular blood sample from the subject (e.g., when a serum sample was used in step (a), the repeated step would use a second serum sample). When the amount or concentration from original step (a) already indicates the presence of liver disease, an increase in the amount or concentration of albumin mRNA at the later time (i.e., from the repeated step (a)) as compared to the original step (a) indicates a worsening of the liver disease, whereas a decrease indicates an improvement of the liver disease.

Similarly, the claimed method may further involve repeating step (a) at a later time using the same type of acellular blood sample from the subject, when the amount or concentration of albumin mRNA from the original step (a) indicates no liver disease. An increase in the amount or concentration of albumin mRNA at the later time (repeated step (a)) as compared to the original step (a) indicates the occurrence of a liver disease, and a substantially lack of change indicates a physiological state of free of the liver disease.

Frequently, an increase or decrease from the standard control in the claimed method is by at least 1 standard deviation. In other cases, such increase or decrease from the standard control may be by at least 2 or even 3 standard deviations.

In another aspect, the present invention provides a kit for diagnosing a liver disease in a subject who has no indication of a liver disease, or a person who is not at risk of developing a liver disease. The kit includes these components: (1) a standard control that provides an average amount or concentration of albumin mRNA in a blood sample of healthy individuals; and (2) two oligonucleotide primers for specifically amplifying at least a section of albumin mRNA. Typically, the kit further contains an instruction manual to aid user in practicing the method of this invention. The kit may also include a polynucleotide probe for specific hybridization with the albumin coding sequence.

In a further aspect, the present invention can also be embodied in a device or a system comprising one or more such devices, which is capable of carrying out all or some of the method steps described herein. For instance, in some cases, the device or system performs the following steps upon receiving an acellular blood sample taken from a subject being tested for detecting a possible liver disease or monitored for changes in liver condition: (a) determining in sample the amount or concentration of albumin mRNA; (b) comparing the amount or concentration with a standard control value; and (c) providing an output indicating whether a liver pathology is present in the subject, or whether there is a change, i.e., worsening or improvement, in the subject's liver condition. In other cases, the device or system of the invention performs the task of steps (b) and (c), after step (a) has been performed and the amount or concentration from (a) has been entered into the device. Preferably, the device or system is partially or fully automated.

In practicing any of the above mentioned aspects of the present invention, the person being tested using the method or kit or device or system of this invention may be one who has no indication of a liver disease, or one who has no known risk of developing a liver disease, or one who has received a liver transplant and shown no symptoms of liver abnormality by conventional testing. In some cases, post-liver transplant patients who previously suffered from hepatocellular carcinoma and the hepatocellular carcinoma recurred subsequent to liver transplantation may be excluded from the practice of this invention.

BRIEF DESCRIPTION OF THE DRAWINGS

FIGS. 11A to 11F are data of serial measurements performed for different patients, each representing one patient. Plasma ALB mRNA concentrations are illustrated by filled circles with solid lines while ALT activity-levels are illustrated by open circles with dashed lines. The plasma ALB mRNA cutoff level of 835 copies/mL is represented by the dotted line.

FIGS. 12A to 12D are data of serial measurements performed for different patients, each representing one patient. Plasma ALB mRNA concentrations are illustrated by filled circles with solid lines while ALT activity-levels are illustrated by open circles with dashed lines. The plasma ALB mRNA cutoff level of 835 copies/mL is represented by the dotted line.

DEFINITIONS

Figure 1:
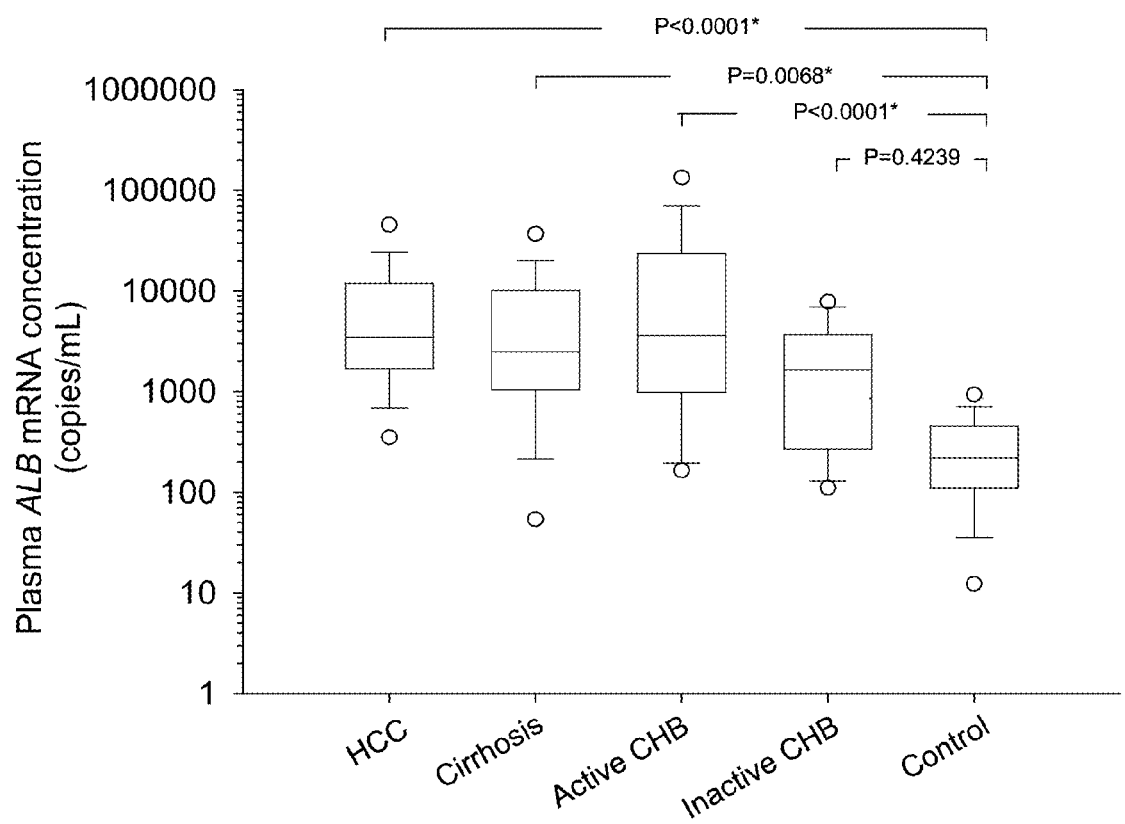
FIG. 1. Box plot of plasma ALB mRNA concentrations. The upper and lower limits of the boxes and the lines across the boxes indicate the $75^{th}$ and $25^{th}$ percentiles and the median, respectively. The whisker caps indicate the $90^{th}$ and $10^{th}$ percentiles. Outliers are illustrated as open circles. The dashed line indicates the cutoff for detecting liver pathologies (835 copies/mL) generated by the ROC analysis. HCC, hepatocellular carcinoma; CHB, chronic hepatitis B.

The term "liver disease," as used in this application, refers to any event or condition that alters normal liver functions in a patient, manifesting its symptoms for any length of time during the patient's life span. Some examples of a liver disease include liver cancer, cirrhosis, liver fibrosis, fatty liver, non-alcoholic steatohepatitis, toxic or mechanical injury to the liver, viral or bacterial infection such as various kinds of hepatitis (e.g., hepatitis A, B, or C), Wilson disease, hemochromatosis, alpha 1-antitrypsin deficiency, or glycogen storage disease. In some cases, hepatocellular carcinoma may be excluded from the liver diseases to be diagnosed for the purpose of this application. Liver diseases are often subclassified as acute or chronic depending on the duration of morbidity. In general, conditions that persist for more than 3 months are considered chronic liver diseases and those lasting less than 3 months are considered acute liver diseases. Acute liver diseases, such as acute hepatitis caused by viral or ischemic injury to the liver, usually presents abruptly but often associated with full restoration of normal liver function. Chronic liver diseases, on the other hand, usually presents insidiously with slow progression but rarely reverts to complete normal liver function.

As liver diseases have varying underlying causes and clinical symptoms, there are numerous different methods for diagnosing these liver diseases. Conventional methods generally include the analysis of serum biochemical markers commonly to assess the level of alanine transaminase (ALT), aspartate transaminase (AST), alkaline phosphatase (ALP), total bilirubin (TBIL), direct bilirubin, or gamma glutamyl transpeptidase (GGT). Alternatively, imaging of the hepatobiliary system by ultrasound, CT scan or MRI, is used to detect structural abnormalities of the liver. A person who is currently not known to have any of those abnormalities, or was never at any time in the past diagnosed with a chronic liver disease, or was known to have been recovered from a previous acute liver disease is a "subject who has no indication of a liver disease." One example of such a person is one who currently is not expected to have an abnormal alanine aminotransferase (ALT) test result because either this person never had an abnormal ALT test result in the past or ALT reverted to normal levels after the last acute liver injury. As carriers of certain hepatic viruses, such as HBV, can be asymptomatic and without overt liver cellular damage to an extent to cause any detectable abnormalities by the conventional liver function tests, a person known to be a carrier of any one of such viruses but never had an abnormal liver function test result is also considered as a "subject who has no indication of a liver disease." A person who not only has no indication of a liver disease but also does not have an immediate family member (parents or siblings) with indication of a liver disease is considered one who is not at risk of developing a liver disease.

The ALT test is routinely employed by the medical professionals. It is usually requested if one is experiencing symptoms of liver disease, including jaundice (yellowish skin or eyes), dark urine, nausea, vomiting, or abdominal pain. It may also be requested to help diagnose infections of the liver such as viral hepatitis or to monitor patients taking medications that cause liver-related side effects. The normal range of ALT levels in the blood is between 5 IU/L to 60 IU/L (International Units per Liter). The normal range for AST levels is 5 IU/L to 43 IU/L.

The term "blood" as used herein refers to a blood sample or preparation from a subject being tested for a possible liver disease or for assessing the physiological state of the subject's liver. An "acellular blood sample" refers to any fraction of blood from which at least 95% of all cells present in whole blood have been removed, and encompasses fractions such as serum and plasma as conventionally defined. Blood samples obtained from different individuals or from the same individual but at different time points following the same processing steps are referred to as "the same type of blood samples."

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in this application, an "increase" or a "decrease" refers to a detectable positive or negative change in quantity from an established standard control. An increase is a positive change preferably at least 2-fold, more preferably at least 5-fold, and most preferably at least 10-fold of the control value. Similarly, a decrease is a negative change preferably at least 50%, more preferably at least 80%, and most preferably at least 90% of the control. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

A "polynucleotide hybridization method" as used herein refers to a method for detecting the presence and/or quantity of a polynucleotide based on its ability to form Watson-Crick base-pairing, under appropriate hybridization conditions, with a polynucleotide probe of a known sequence. Examples of such hybridization methods include Southern blotting and Northern blotting.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the albumin coding sequence. At least one of the PCR primers for amplification of a polynucleotide sequence is sequence-specific for the sequence.

The term "digital polymerase chain reaction" as used herein refers to a refined version of conventional polymerase chain reaction (PCR) methods that can be used to directly quantify and clonally amplify nucleic acids including DNA, cDNA or RNA, such that the amount of target nucleic acid can be directly quantitatively measured. Digital PCR achieves this direct quantitative measurement by capturing or isolating each individual nucleic acid molecule present in a sample within many separate reaction chambers that are able to localize and concentrate the amplification product to detectable levels. After PCR amplification, a count of chambers containing PCR end-product is a direct measure of the absolute nucleic acids quantity. The capture or isolation of individual nucleic acid molecules, typically by way of dilution, may be effected in capillaries, microemulsions, arrays of miniaturized chambers, or on nucleic acid binding surfaces. The basic methodology of digital PCR is described in, e.g., Sykes et al., *Biotechniques* 13 (3): 444-449, 1992.

The term "molecular counting" as used herein refers to any method that allows quantitative measurement of the number of a molecule or molecular complex, often the relative number in the context of other co-existing molecules or complexes of distinct characteristics. Various methods of molecular counting are described in, e.g., Leaner et al., *Analytical Chemistry* 69:2115-2121, 1997; Hirano and Fukami, *Nucleic Acids Symposium Series* No. 44:157-158, 2000; Chiu et al., *Trends in Genetics* 25:324-331, 2009; and U.S. Pat. No. 7,537,897.

"Standard control" as used herein refers to a predetermined amount of a polynucleotide sequence, e.g., albumin mRNA, that is present in an established sample, e.g., an acellular blood sample. The standard control value is suitable for the use of a method of the present invention, to serve as a basis for comparing the amount of albumin mRNA that is present in a test sample. An established sample serving as a standard control provides an average amount of albumin mRNA that is typical for a particular blood sample (particularly an acellular blood sample, e.g., serum or plasma) of an average, healthy human without any liver disease as conventionally defined. A standard control value may vary depending on the nature of the sample as well as other factors such as the gender, age, ethnicity of the subjects based on whom such a control value is established.

The term "average," as used in the context of describing a human who is healthy, free of any liver disease as conventionally defined, refers to certain characteristics, especially the amount of albumin mRNA found in the person's blood or any acellular fractions of the blood, e.g., serum or plasma, that are representative of a randomly selected group of healthy humans who are free of any liver pathologies. This selected group should comprise a sufficient number of humans such that the average amount of albumin mRNA in the blood or blood fraction among these individuals reflects, with reasonable accuracy, the corresponding albumin mRNA amount in the general population of healthy humans. In addition, the selected group of humans generally have a similar age to that of a subject whose blood sample is tested for indication of a potential liver disorder. The preferred age for practicing the present invention may vary depends on the liver disease/disorder that is being screened for. Moreover, other factors such as gender, ethnicity, medical history are also considered and preferably closely matching between the profiles of the test subject and the selected group of individuals establishing the "average."

The term "amount" as used in this application refers to the quantity of a polynucleotide sequence of interest, e.g., albumin mRNA, present in a sample. Such quantity may be expressed in the absolute terms, i.e., the total quantity of the polynucleotide sequence in the sample, or in the relative terms, i.e., the concentration of the polynucleotide sequence in the sample.

DETAILED DESCRIPTION OF THE INVENTION

I. Introduction

The analysis of circulating nucleic acids in plasma offers an avenue for noninvasive monitoring of a variety of physiological and pathological conditions (Lo et al., *Ann N Y Acad Sci* 2004; 1022:135-139; Chan et al. *Ann Clin Biochem* 2003; 40:122-30). Numerous applications based on the detection of circulating cell-free nucleic acids in human plasma, ranging from those for the management of malignancies (Anker et al., *Int J Cancer* 2003; 103:149-52), pregnancy-associated conditions (Lo et al., *Nat Rev Genet* 2007; 8:71-7), organ transplantation (Lo et al., *Lancet* 1998; 351:1329-30) and trauma (Lo et al., *Clin Chem* 2000; 46:319-23; Chiu et al., *Acta Neurochir Suppl* 2005; 95:471-4), have been reported. The fundamental principle underlying these applications relate to the plasma detection of extracellular nucleic acid molecules derived from diseased organs. Disease-specific genetic signatures that could be exploited from circulating DNA analysis include the detection of disease-related pathogens (Chan et al., *Clin Chem* 2005; 51:2192-5), disease-specific mutations, sex and polymorphism differences between a fetus and its mother or a transplant donor and recipient.

In addition to circulating DNA, cell-free plasma RNA analysis offers another dimension of opportunity for the development of pathology-related markers (Lo et al., *Ann N Y Acad Sci* 2004; 1022:135-139; Anker et al., *Clin Chem* 2002; 48:1210-1). Expression profiles unique to an organ or disease could be targeted as the specific nucleic acid signature for plasma detection. Tumor- (Chen et al., *Clin Cancer Res* 2000; 6:3823-6) and placenta-derived RNA species (Ng et al., *Proc Natl Acad Sci USA* 2003; 100:4748-53) have been successfully detected from plasma with potential for disease assessment (Ng et al., *Clin Chem* 2003; 49:727-31). The present inventors have explored the possibility of detecting circulating liver-derived mRNA for the assessment of liver pathologies.

There is much evidence to suggest that circulating DNA and RNA are released upon cell death (Jahr et al., *Cancer Res* 2001; 61:1659-65). As albumin is the most abundant protein of the body and is synthesized by the liver, the inventors hypothesized that ALB mRNA may be detectable in human plasma and is possibly a sensitive marker of liver pathologies. Indeed, previous studies reported the detection of ALB mRNA in peripheral whole blood and the peripheral mononuclear cell fraction (Hillaire et al., *Gastroenterology* 1994; 106:239-42; Kar et al., *Hepatology* 1995; 21:403-7; Muller et al., *Hepatology* 1997; 25:896-9; Barbu et al., *Hepatology* 1997; 26:1171-5; Gion et al., *Hepatology* 1998; 28:1663-8; Peck-Radosavljevic et al., *Liver Transplant Oncology Group. J Hepatol* 1998; 28:497-503; Wong et al., *Br J Cancer* 1997; 76:628-33; Wong et al., *Cancer Lett* 2000; 156:141-9; Bastidas-Ramirez et al., *Hepatol Res* 2002; 24:265.11) of human subjects. However, these studies reported a mixed level of success with detection rates of blood ALB mRNA below 100% from patients with hepatocellular carcinoma (HCC), cirrhosis, hepatitis and healthy controls. Yet, Kudo et al., (*J Vet Med Sci* 2008; 70:993-5) recently reported the presence and correlation of plasma ALB mRNA concentration with hepatic injury in rats.

Blood cells are able to "illegitimately" transcribe genes known to be predominantly expressed by other cell types (Lambrechts et al., *Ann Oncol* 1998; 9:1269-76) and the present inventors have previously demonstrated that blood cells are the major contributors of plasma nucleic acids (Lui et al., *Clin Chem* 2002; 48:421-7). Therefore the inventors first aimed to determine whether plasma or whole blood ALB mRNA were derived from the liver, and second, after confirming the liver origin of plasma ALB mRNA, it was determined whether quantitative aberrations could be detected in a variety of liver pathologies. In order to achieve the first aim, a previously described RNA-single nucleotide polymorphism (SNP) strategy (Lo et al., *Nat Med* 2007; 13:218-23; Chan et al., *Clin Chem* 2007; 53:1874-6) was used to genotype ALB mRNA molecules found in the circulation of recipients of liver or bone marrow transplantations from donors who were genotypically different for the targeted ALB coding SNP.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of a genetic marker or genomic sequence used in this invention, e.g., the polynucleotide sequence of the albumin gene, and synthetic oligonucleotides (e.g., primers) can be verified using, e.g., the chain termination method for sequencing double-stranded templates of Wallace et al., *Gene* 16: 21-26 (1981).

III. Acquisition of Blood Samples and Extraction of mRNA

The present invention relates to analyzing the amount of albumin mRNA found in a person's blood, especially an acellular blood sample, as a non-invasive means to detect the presence and/or to monitor the progress of a liver disease or disorder. Thus, the first steps of practicing this invention are to obtain a blood sample from a test subject and extract mRNA from the sample.

A. Acquisition of Blood Samples

A blood sample is obtained from a person to be tested or monitored for a liver condition or disorder using a method of the present invention. Collection of blood from an individual is performed in accordance with the standard protocol hospitals or clinics generally follow. An appropriate amount of peripheral blood, e.g., typically between 5-50 ml, is collected and may be stored according to standard procedure prior to further preparation.

B. Preparation of Blood Samples

The analysis of albumin mRNA found in a patient's blood sample according to the present invention may be performed using, e.g., the whole blood, or more often in an acellular sample such as serum, or plasma. The methods for preparing serum or plasma from maternal blood are well known among those of skill in the art. For example, a subject's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum may be obtained with or without centrifugation-following blood clotting. If centrifugation is used though it is typically, though not exclusively, conducted at an appropriate speed, e.g., 1,500-3,000×g. Plasma or serum may be subjected to additional centrifugation steps before being transferred to a fresh tube for RNA extraction. Any other method of producing an acellular sample from the whole blood is also appropriate for the purpose of this invention, so long as the method generates an acellular blood sample that is substantially cell-free, e.g., having removed at least 90%, 95%, 98%, or 99% or more of all cells originally present in the whole blood sample.

C. Extraction and Quantitation of RNA

There are numerous methods for extracting mRNA from a biological sample. The general methods of mRNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a female test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of mRNA Level

Once mRNA is extracted from a sample, the amount of albumin mRNA may be quantified. The preferred method for determining the mRNA level is an amplification-based method, e.g., by polymerase chain reaction (PCR).

Prior to the amplification step, a DNA copy (cDNA) of the albumin mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention. One of skill in the art will recognize, however, that amplification of these mRNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA markers in maternal blood. For a review of branched-DNA signal amplification for direct quantitation of nucleic acid sequences in clinical samples, see Nolte, *Adv. Clin. Chem.* 33:201-235, 1998.

2. Other Quantitative Methods

The albumin mRNA can also be detected using other standard techniques, well known to those of skill in the art. Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well known techniques (see, e.g., Sambrook and Russell, supra), the presence of a band of the same size as the standard comparison is an indication of the presence of a target mRNA, the amount of which may then be compared to the control based on the intensity of the band. Alternatively, oligonucleotide probes specific to albumin mRNA can be used to detect the presence of such mRNA species and indicate the amount of mRNA in comparison to the standard comparison, based on the intensity of signal imparted by the probe.

Sequence-specific probe hybridization is a well known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, In situ *Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255:137-149, 1983.

IV. Establishing a Standard Control

In order to establish a standard control for practicing the method of this invention, a group of healthy persons free of any liver disease as conventionally defined is first selected. These individuals are within the appropriate parameters, if applicable, for the purpose of screening for and/or monitoring liver disorders or diseases such as cirrhosis, liver fibrosis, hepatitis and others using the methods of the present invention. Optionally, the individuals are of same gender, similar age, or similar ethnic background.

The healthy status of the selected individuals is confirmed by well established, routinely employed methods including but not limited to general physical examination of the individuals and general review of their medical history.

Furthermore, the selected group of healthy individuals must be of a reasonable size, such that the average amount/concentration of albumin mRNA in the blood obtained from the group can be reasonably regarded as representative of the normal or average level among the general population of healthy people. Preferably, the selected group comprises at least 10 human subjects.

Once an average value for the albumin mRNA is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gender, or ethnic background.

V. Kits

The invention provides compositions and kits for practicing the methods described herein to assess the state of liver physiology or pathology in a subject, which can be used for various purposes such as detecting or diagnosing the presence of a liver disease, and monitoring the progression of a liver disease in a patient, especially one who has no indication of any liver injury, disorder, or disease.

Kits for carrying out assays for determining albumin mRNA level typically include at least one oligonucleotide useful for specific hybridization with the albumin coding sequence or complementary sequence. Optionally, this oligonucleotide is labeled with a detectable moiety. In some cases, the kits may include at least two oligonucleotide primers that can be used in the amplification of albumin mRNA by PCR, particularly by RT-PCR.

Typically, the kits also provide instruction manuals to guide users in analyzing test samples and assessing the state of liver physiology or pathology in a test subject.

EXAMPLES

The following examples are provided by way of illustration only and not by way of limitation. Those of skill in the art will readily recognize a variety of non-critical parameters that could be changed or modified to yield essentially the same or similar results.

Example 1

I. Materials and Methods

Participants

Between June 2006 and April 2008, participants were recruited from the Prince of Wales Hospital, Hong Kong, including (i) patients with a range of liver complications who attended the Departments of Medicine and Therapeutics, and Clinical Oncology; (ii) patients who previously received liver transplantation (LT) at the Department of Surgery and the paired living donors; (iii) patients who received bone marrow transplantation (BMT) at the Department of Pediatrics; and (iv) healthy individuals. Ethical approval was obtained from the institutional review board, and informed consent was obtained from all participants or responsible guardians.

Ten mL of peripheral blood was collected into EDTA-tubes. Either buccal cells or hair follicle cells were also collected from the BMT patients. For those participants who have received cadaveric LT, archived liver biopsy tissue specimens of deceased donors were retrieved.

Sample Collection and Processing

Immediately after blood collection, samples were kept at 4° C. and processed within 4 h. After gently mixing the blood sample, 0.3 mL of whole blood was mixed with 0.9 mL of TRIzol LS reagent (Invitrogen, Carlsbad, Calif.). Plasma was harvested by a double-centrifugation protocol (Chiu et al., Clin Chem 2001; 47:1607-13). Buffy coat was isolated after the first centrifugation step and re-centrifuged at 230 g for 5 min at 4° C. to remove any residual plasma. All samples were stored until nucleic acid extraction as described in this section.

ALB Genotyping

Figure 5:
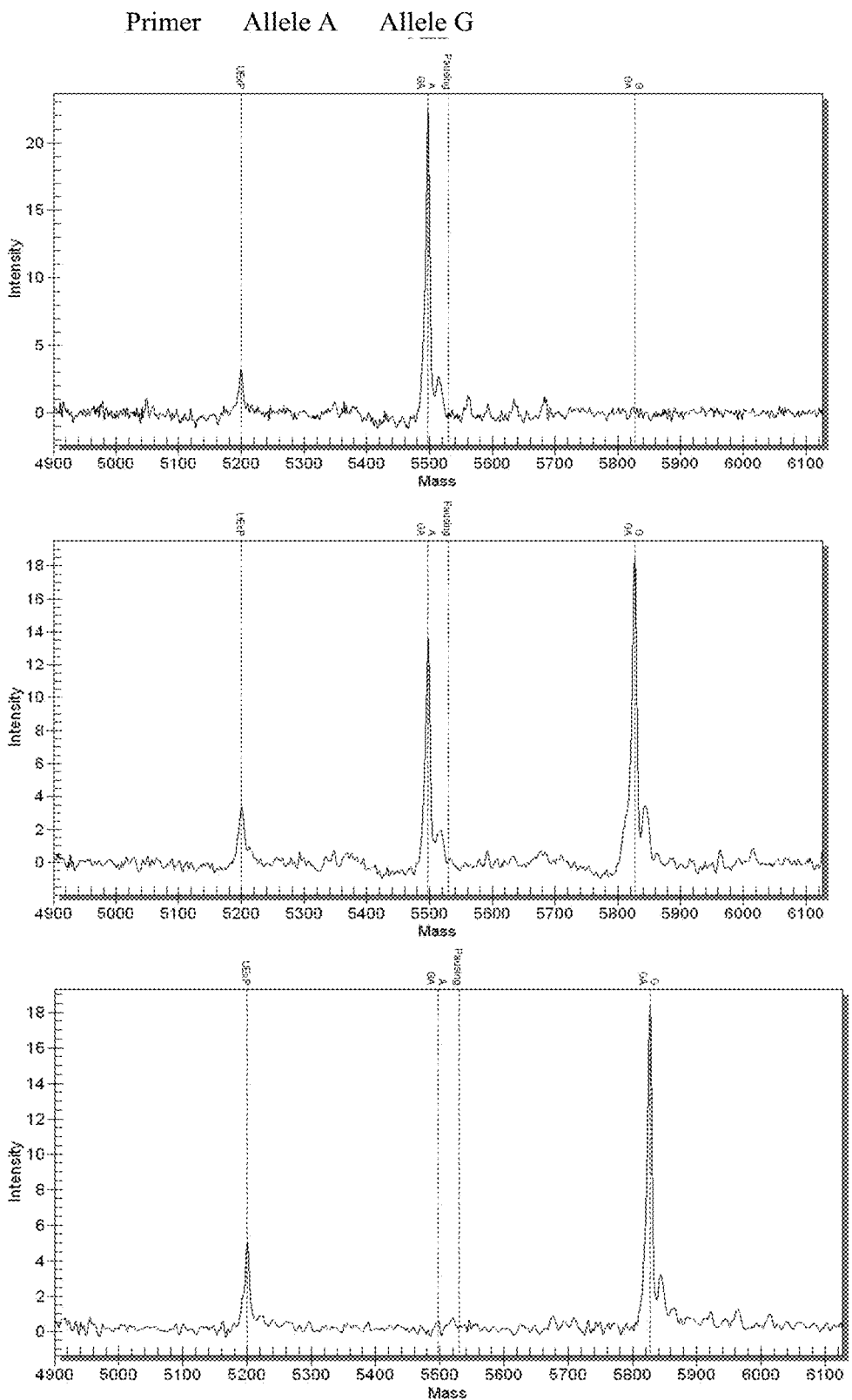
FIG. 5. Mass spectra obtained for the genotyping of the ALB SNP, rs962004. The SNP alleles are resolved by the differences in the molecular masses of the extension products. The positions for peaks representing the unextended primer, the extended A and G alleles, respectively, are as marked. The x-axis depicts the mass measured in Daltons, while the y-axis depicts the intensity of ionic current measured in arbitrary units. The hME assay can be applied to the genotyping of both DNA and RNA products. Samples that were homozygous for the A-allele, heterozygous and homozygous for the G-allele are shown in the upper, middle and lower panels, respectively.

A SNP, rs962004, within the coding region of ALB was targeted. By DNA sequencing of ten unrelated individuals, it was found that the SNP has a minor allele frequency of 0.37. Genotyping was performed by a primer extension reaction using a homogenous MassEXTEND (hME) (Sequenom, San Diego, Calif.) assay. Extension products for each SNP allele would demonstrate distinct masses that could be resolved by matrix-assisted laser desorption/ionization time-of-flight mass spectrometry analysis (See FIG. 5). Details of the SNP analysis can be found in Table 3.

Genotypes of LT recipients and liver donors were determined using buffy coat DNA. For cadaveric LT cases, the ALB genotypes of the deceased donors were determined from the archived liver biopsy tissue DNA. For BMT recipients, their original ALB genotypes were detected from DNA of buccal cells or hair follicles. The ALB genotypes of the bone marrow donors were assessed using the buffy coat DNA of recipients after BMT. Genotypes of ALB mRNA in plasma or whole blood of the transplantation recipients were determined using the same genotyping assay on reverse transcribed ALB mRNA.

Quantification of ALB mRNA Transcript in Plasma

One-step reverse transcription-quantitative real-time PCR (RT-qPCR) was used to measure the plasma ALB mRNA concentrations. The intron-spanning assay for ALB mRNA quantification was designed to amplify a 78-bp ALB amplicon across exon 1 and exon 2 at the 5' region (GenBank Accession No. NM_000477.3) and the sequences are summarized in Table 4. Calibration curves for absolute ALB mRNA quantification were prepared by subjecting serial dilutions of HPLC-purified single-stranded synthetic DNA oligonucleotides (Sigma-Proligo, Singapore) specifying the targeted ALB amplicon (Wong et al., Clin Chem 2005; 51:1786-95), with concentrations ranging from 3 copies to $3 \times 10^6$ copies per well of reaction. The amplification of ALB mRNA was monitored by an ABI Prism 7900 Sequence Detector (Applied Biosystems, Foster City, Calif.) and the Sequence Detection Software version 2.2 (Applied Biosystems). The median PCR efficiency was 88.3% (SD: 6%, range: 81.1%-98.8%) calculated from the calibration curves with a median slope of −3.64 (SD: 0.18, range: 3.35-3.88), y-intercept at 40.8 (SD: 1.86, range: 38.1-43.5) and correlation coefficient of 0.9958 (SD: 0.0026, range: 0.9905-0.9986). Absolute concentrations of ALB mRNA in plasma were expressed as copies/mL.

Assessment of Liver Function

Plasma analysis for albumin, total bilirubin, alkaline phosphatase, alanine transaminase (ALT) and alpha-fetoprotein was performed by the Chemical Pathology laboratory of the Prince of Wales Hospital, Hong Kong, using a DPE Modular Analytics system (Roche Diagnostics). Hepatitis B virus (HBV) DNA was quantified in serum of patients with chronic hepatitis B (CHB) infection as previously described (Chan et al., J Med Virol 2002; 68:182-7; Loeb et al., Hepatology 2000; 32:626-629). Concentrations>10,000 copies/mL was considered as evidence for active viral replication (Chan et al., B. J Clin Microbiol 2003; 41:4693-5).

Statistical Analysis

Statistical analyses were performed using the SPSS version 15.0 software (SPSS Inc., Chicago, Ill.). Plasma ALB mRNA concentrations were compared between patient and control groups by the Kruskal-Wallis H test and Dunn's test as appropriate. Correlations between plasma ALB mRNA concentrations and other parameters were determined by the Spearman's rank correlation. A p value of less than 0.05 was considered as statistically significant and all probabilities were two tailed. An outlier was identified when the plasma ALB mRNA concentration of the sample was greater than 3 standard deviations from the mean of the corresponding group. ROC curve was constructed to determine the area under the curve (AUC). Sensitivity and specificity were calculated at the optimal plasma ALB mRNA concentration cutoff point for distinguishing patients with liver complications from healthy individuals.

Sample Collection and Preparation

To harvest plasma, each blood sample was first centrifuged at 1 600 g for 10 min at 4° C. (Centrifuge 5810R, Eppendorf, German). The supernatants were carefully transferred into plain polypropylene tubes and re-centrifuged at 16 000 g for 10 min at 4° C. (Centrifuge 5417R, Eppendorf) (Chiu et al., *Clin Chem* 2001; 47:1607-13). The plasma was then transferred into fresh polypropylene tubes without disturbing the underlying pellet. Every 1.6 mL of plasma was then mixed with 4.8 mL of TRIzol LS reagent (Invitrogen) and stored at −80° C. until extraction (Heung et al., *Prenat Diagn* 2009; 29:277-9).

RNA Extraction

Each plasma-TRIzol LS mixture was thawed and mixed with 1.28 mL of chloroform. The RNA lysate was separated into different phases by centrifugation at 12 000 g for 15 min at 4° C. The aqueous layer was then carefully transferred to fresh polypropylene tubes. For RNA precipitation, one volume of 700 mL/L ethanol was added to one volume of the aqueous layer. The mixture was applied to a spin column of the RNeasy Mini Kit (Qiagen, Valencia, Calif.) and processed according to the manufacturer's protocols. Total RNA was eluted in 50 µl of RNase-free water. All RNA samples were pre-treated with Amplification Grade Deoxyribonuclease I (Invitrogen) according to the manufacturer's instructions and then stored at −80° C. until use.

DNA Extraction

DNA extraction of buffy coat, buccal cells, hair follicle cells and paraffinized liver biopsied tissue was performed either with the QIAamp Blood Mini Kit (Qiagen) or QIAamp DNA Mini Kit (Qiagen) as appropriate and recommended by the manufacturer. All DNA samples were eluted in 50 µL of double distilled water and then be stored at −20° C. until use.

RNA-SNP Analysis by MassARRAY™ Homogenous MassEXTEND™ (hME) Assay Followed by Mass Spectrometric Detection Reverse Transcription—

The RNA samples were reverse transcribed by a thermostable avian reverse transcriptase (ThermoScript™ Reverse Transcriptase, Invitrogen) with a gene-specific primer (Integrated DNA Technologies; See Table 3) in 0.5 µM of final concentration at 55° C. for 1 h.

PCR Amplification—

For the amplification of reverse transcribed cDNA, each reaction contained 0.6× HotStar Taq PCR buffer with 0.9 mM $MgCl_2$ (Qiagen), 25 µM each of dATP, dGTP, and dCTP, 50 µM dUTP (Applied Biosystems). For the amplification of DNA, each reaction contained 1× HotStar Taq PCR buffer with 1.5 mM $MgCl_2$ (Qiagen), an additional 1 mM $MgCl_2$ (Qiagen), 50 µM each of dATP, dGTP, and dCTP, 100 µM dUTP (Applied Biosystems). For all PCRs, forward and reverse primers (Integrated DNA Technologies, Coralville, Iowa; See Table 4) were at 200 nM and HotStar Taq Polymerase (Qiagen) was at 0.5 U of final concentration. The PCR was initiated at 95° C. for 15 min, followed by denaturation at 95° C. for 20 s, annealing at 56° C. for 30 s, extension at 72° C. for 1 min for 45 cycles, and, finally, incubation at 72° C. for 3 min.

Base Extension—

PCR products were subjected to shrimp alkaline phosphatase (SAP) treatment with 0.6 U of shrimp alkaline phosphatase (Sequenom), 0.34 µl of MassARRAY™ Homogenous MassEXTEND™ (hME) buffer (Sequenom), and 3.06 µl of water. The mixture was incubated at 37° C. for 40 min followed by 85° C. for 5 min to remove excess dNTPs. Genotyping was performed with hME assays (Sequenom). For the RNA SNP genotyping, 9 µl of base extension reaction cocktail containing 1.2 µM extension primer (Integrated DNA Technologies; See Table 3), 1.15 U of Thermosequenase (Sequenom), and 64 µM each of ddATP, ddCTP and dGTP (Sequenom) were added to 5 µL of the SAP-treated PCR products. For the DNA SNP genotyping, 4 µL of base extension reaction cocktail containing 0.771 µM extension primer (Integrated DNA Technologies; see Table I), 1.15 U of Thermosequenase (Sequenom), and 64 µM each of ddATP, ddCTP and dGTP (Sequenom) were added to 10 µL of the SAP-treated PCR products. The reaction conditions were 94° C. for 2 min, followed by 85 cycles of 94° C. for 5 s, 52° C. for 5 s, and 72° C. for 5 s for RNA-SNP genotyping. For DNA-SNP genotyping 75 cycles of the same thermal profile was used for the primer extension reaction.

Liquid Dispensing and MALDI-TOF MS Data Analysis—

The final base extension product was cleaned up by the addition of 12 mg of Clean Resin (Sequenom) and 24 µL of water. The mixtures were mixed in a rotator for 20 min. After centrifugation at 361 g for 5 min, 10 nL of reaction solution was dispensed onto a SpectroCHIP (Sequenom) by a MassARRAY Nanodispenser S (Sequenom). A MassARRAY Analyzer Compact Mass Spectrometer (Bruker, Madison, Wis.) was used for data acquisition from the SpectroCHIP. Mass spectrometric data were automatically imported into a MassARRAY Typer (Sequenom) database for analysis.

Detection of ALB mRNA Transcript in Plasma by Real-Time Quantitative PCR

The assay for ALB mRNA quantification was designed using Primer Express v2.0 (Applied Biosystems). The forward primer and reverse primer were located in exon 1 and exon 2, respectively and were synthesized by Integrated DNA Technologies. The fluorogenic probe (Applied Biosystems, Foster City, Calif.) spanned the junction between exons 1 and 2 to prevent the amplification of contaminating genomic DNA (See Table 4). In silico specificity screen and sequence alignment were performed to ensure that the amplicon was specific to the targeted location on ALB and had no splice variant.

The reverse transcription-quantitative real-time PCR reactions were set up manually according to the manufacturer's instructions (TaqMan EZ RT-PCR Core Reagents; Cat. No. N8080236; Applied Biosystems) in a reaction volume of 25 µL. The final concentrations of each component per reaction were as follows: the EZ buffer in 1×, manganese acetate solution in 3 mM, dNTPs in 300 µM, AmpErase Uracil N-glycosylase in 0.25 unit, forward primer in 400 µM, reverse primer in 400 µM, probe in 200 µM, rTth DNA polymerase in 2.5 units and no additive was used. For amplification, 3 µl of extracted plasma RNA was added into each well of the 96-well reaction plates (MicroAmp Optical 96-Well Reaction Plate; Cat No. N8010560; Applied Biosystems). The thermal profile used for the ALB mRNA analysis was as follows: the reaction was initiated at 50° C. for 2 min for the included uracil N-glycosylase to act, followed by reverse transcription at 60° C. for 30 min. After a 5-min denaturation at 95° C., 45 cycles of PCR were carried out with denaturation at 94° C. for 20 s and 1 min of annealing/extension at 58° C. Each sample was analyzed in duplicate, and the corresponding calibration curve was run in parallel with each analysis.

Multiple water blanks and liver tissue RNA were included in every analysis as negative and positive controls, respectively. Samples were also tested to ensure that they were negative for DNA by substituting the rTth polymerase with the AmpliTaq Gold enzyme (Applied Biosystems). No amplification was observed in all negative water blanks and "No-RT" control analysis, indicating the specificity of the assay for mRNA. Specificity of the PCR product was validated by gel electrophoresis analysis. The limit of detection for ALB analysis was found to be 3 copies per reaction well because 98% of 40 duplicate wells [=80 wells in total], containing 3 copies per reaction well, were successfully detected with a median (range) threshold cycle of 38.6 (37.8-44.3). Intra-assay CV of the ALB mRNA assay was evaluated by measuring a sample with ALB mRNA concentration adjusted to 835 copies/mL, which was defined as the cutoff level of plasma ALB mRNA concentration for identifying patients with liver disease from healthy controls by the ROC analysis, in 20 duplicate wells on the same reaction plate. The mean ALB mRNA concentration detected from the replicates was 855 copies/mL with SD of 85 copies/mL and CV of 9.97%.

II. Results

Origin of ALB mRNA in Circulation

To determine if ALB mRNA in plasma and whole blood is liver-derived, a RNA-SNP assay was developed to genotype the ALB mRNA molecules found in the circulation of LT and BMT recipients. The analysis was focused on informative donor-recipient pairs who were defined as donors who bore a different genotype for the interrogated ALB SNP than their corresponding recipients. After liver transplantation, the genotype corresponding to that of the donor should be observed for the ALB mRNA molecules found in the circulation of the recipient if the ALB mRNA were genuinely liver-derived. Alternatively, if other tissue sources contributed to the pool of circulating ALB mRNA, the ALB genotype of the recipient should be detectable. To demonstrate that hematopoietic cells could be a contaminating source of circulating ALB mRNA, a similar RNA-SNP analysis was performed for recipients of BMT. Similarly, the circulating ALB mRNA molecules would exhibit the genotype of the bone marrow donor if hematopoietic cells contributed ALB mRNA to the circulation.

Twenty-nine (29) LT cases were studied where nine (9) recipients obtained livers from their living relatives and the remaining from cadavers. Fifteen (15) of these donor-recipient pairs were deemed informative by showing distinct ALB genotypes between the donor and recipient. Table 1 summarizes the genotyping data of the informative donors and recipients. Among the informative cases, the ALB mRNA genotypes detected in the plasma of the recipients after transplantation were different from their original genotypes and corresponded to that of the liver donors.

Five of the 20 BMT cases recruited were informative and the genotyping data are summarized in Table 1. There was no change in the ALB mRNA genotypes in plasma of the recipients before and after BMT. Thus, the donor's bone marrow was not a significant contributor of ALB mRNA in the recipient's plasma.

Besides plasma, RNA-SNP analysis was also performed on ALB mRNA in whole blood collected from the informative LT and BMT recipients after transplantation. Twelve (12) informative LT cases and four (4) informative BMT cases consented to this analysis and the genotyping data are shown in Table 1. Unlike the plasma data, contributions from the bone marrow donors (cases B8 and B10) and the LT recipients (cases L8, L18, L23, L24 and L25) were observed in the whole blood ALB mRNA. In summary, plasma ALB mRNA was liver-derived while ALB mRNA in whole blood was not liver-specific.

Quantitative Analysis of Plasma ALB mRNA

After confirming that plasma ALB mRNA was liver-specific, the inventors assessed its concentration in plasma obtained from 107 patients with a spectrum of liver complications and 207 healthy individuals. Among the patients, 35 were confirmed to have HCC, 25 had biopsy-proven liver cirrhosis, 24 had CHB with serum HBV DNA concentrations>10,000 copies/mL, i.e., active viral replication, and 23 had CHB serum HBV DNA concentrations<10,000 copies/mL, i.e., inactive viral replication. All healthy individuals were tested to be HBsAg negative and had liver function test parameters within reference intervals according to standard plasma biochemical tests.

Information about the demographics, biochemical testing, virological investigations and the median plasma ALB mRNA concentrations of the participants are summarized in Table 2. Plasma ALB mRNA was detected in 308 of the 314 participants (98.1%) with negative readings for one patient and five controls. Concentrations of plasma ALB mRNA of all the groups are shown in FIG. 1. Plasma ALB mRNA concentrations were statistically significantly different among the participant groups (P<0.0001, Kruskal-Wallis test). Subgroup analysis showed that patients with HCC (P<0.0001), liver cirrhosis (P=0.0068) and active CHB (P<0.0001) had statistically significant elevation in plasma ALB mRNA concentrations when compared to controls. There was no statistically significant difference in plasma mRNA concentrations between controls and patients with inactive CHB (P=0.4239, Dunn's test). These data further support that persons with inactive CHB generally have liver status similar to that of healthy controls.

Figure 2:
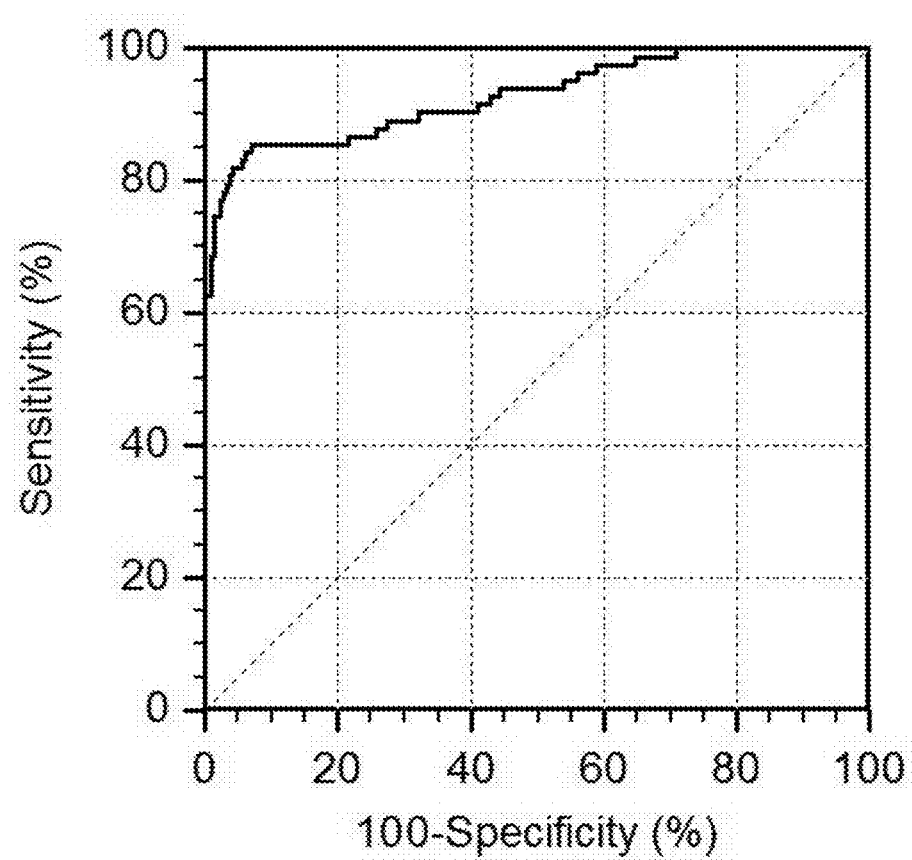
FIG. 2. Receiver-operating characteristic curve for the detection of liver pathologies by plasma ALB mRNA quantification.

ROC curve analysis was performed to assess if plasma ALB mRNA concentration would be an effective indicator of liver pathologies (FIG. 2). The AUC suggested that the diagnostic efficacy of using plasma ALB mRNA as an indicator of liver pathologies was 92.9%. By using 835 copies/mL of plasma ALB mRNA as a cutoff, the sensitivity and specificity for detecting any one of the assessed liver pathologies were 85.5% and 92.8% respectively.

Figure 3:
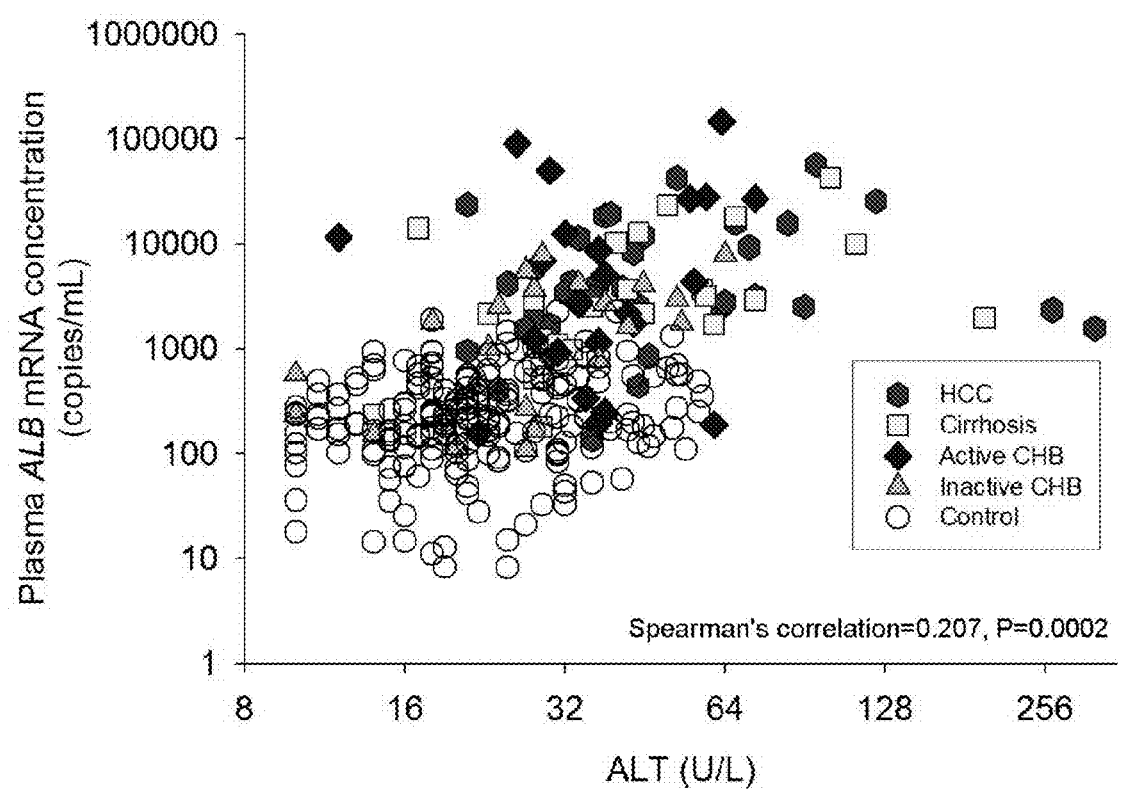
FIG. 3. Correlation between plasma ALB mRNA and alanine transaminase concentrations. HCC, hepatocellular carcinoma; CHB, chronic hepatitis B.

Relationship Between Plasma ALB mRNA Concentrations and Conventional Liver Function Test Parameters Considering data from all the study participants (patients and controls), plasma ALB mRNA concentration weakly correlated with plasma total bilirubin (r=0.133, P=0.018, Spearman's correlation), alkaline phosphatase (r=0.126, P=0.0255) and ALT (r=0.207, P=0.0002; FIG. 3).

Figure 4:
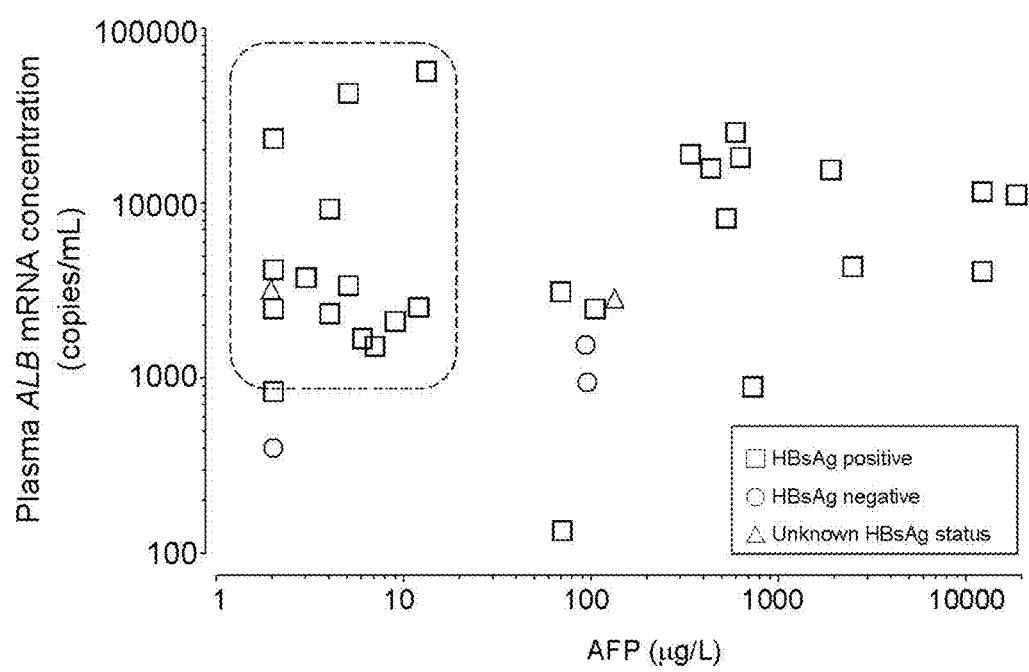
FIG. 4. Correlation between plasma ALB mRNA and serum alpha-fetoprotein in hepatocellular carcinoma patients. The inset encloses those patients with alpha-fetoprotein (AFP)<20 μg/L but plasma ALB mRNA concentration>835 copies/mL.

Of 107 patients, only 23 (21.5%) patients had elevated ALT levels (>58 IU/L), whilst 62 (73.8%) patients had plasma ALB mRNA concentrations>835 copies/mL. For the 35 patients with HCC confirmed by liver biopsy, only 17 (49%) patients had elevated alpha-fetoprotein levels (>20 µg/L) (Sherman et al., *Hepatology* 1995; 22:432-8). However, 32 (91.4%) of these patients had elevated plasma ALB mRNA concentrations as shown in FIG. 4.

Plasma ALB mRNA Analysis in Subjects with Normal Liver Function

It was remarkable to note that plasma ALB mRNA was elevated in patients with liver disease but normal plasma ALT or AFP levels. ALT is a customarily used biochemical marker to indicate hepatocellular damage. These data indicate that ALB mRNA is more sensitive than plasma ALT for detection of liver diseases. In view of these findings, the data were reanalyzed to only include subjects with normal plasma ALT. The reference range for normal plasma ALT provided by the testing laboratory involved in this study was <58 U/L.

Figure 6:
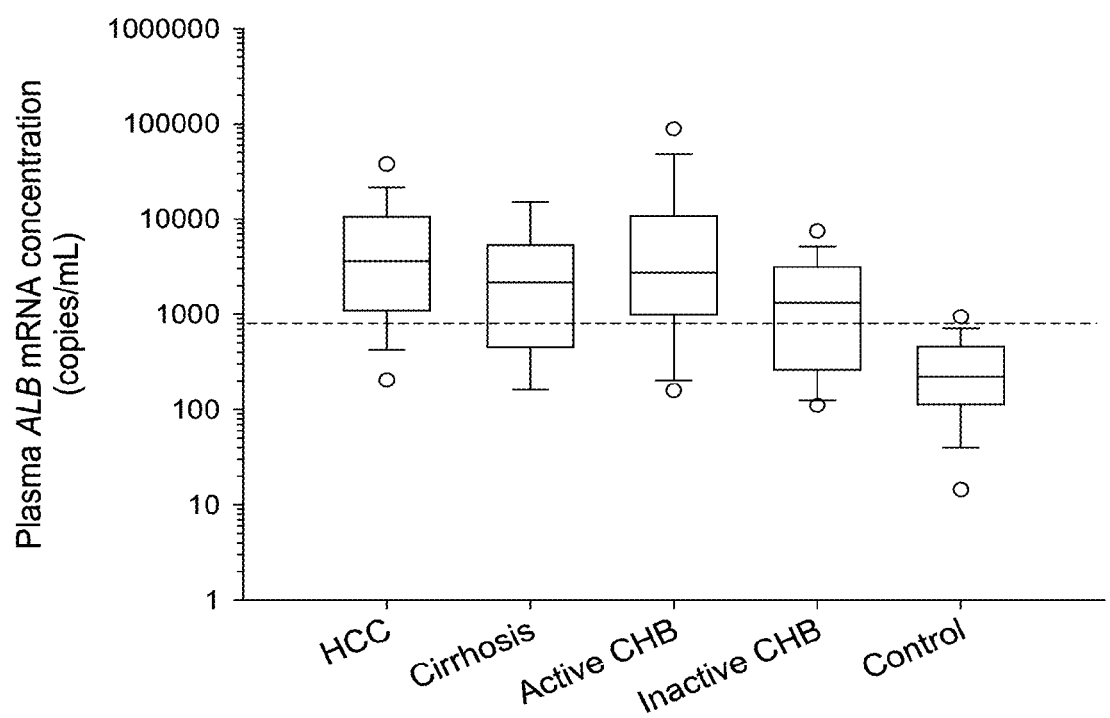
FIG. 6. Box plot of plasma ALB mRNA concentrations in participants without elevated plasma ALT. The upper and lower limits of the boxes and the lines across the boxes indicate the $75^{th}$ and $25^{th}$ percentiles and the median, respectively. The whisker caps indicate the $90^{th}$ and $10^{th}$ percentiles. Outliers are illustrated as open circles. The dashed line indicates the cutoff for detecting liver pathologies (835 copies/mL) generated by the ROC analysis. HCC, hepatocellular carcinoma; CHB, chronic hepatitis B.

A total of 291 study participants had normal plasma ALT. This represented 93% of all participants. Information about the demographics, biochemical testing, virological investigations and the median plasma ALB mRNA concentrations of this subgroup of participants are summarized in Table 5. Concentrations of plasma ALB mRNA of all the groups with normal plasma ALT are shown in FIG. 6. Plasma ALB mRNA concentrations were statistically significantly different among the subgroups (P<0.0001, Kruskal-Wallis test). Further analysis showed that patients with HCC (P<0.0001), liver cirrhosis (P=0.0094) and active CHB (P<0.0001) had statistically significant elevation in plasma ALB mRNA concentrations when compared to controls. There was no statistically significant difference in plasma mRNA concentrations between controls and patients with inactive CHB (P=0.2723, Dunn's test).

Figure 7:
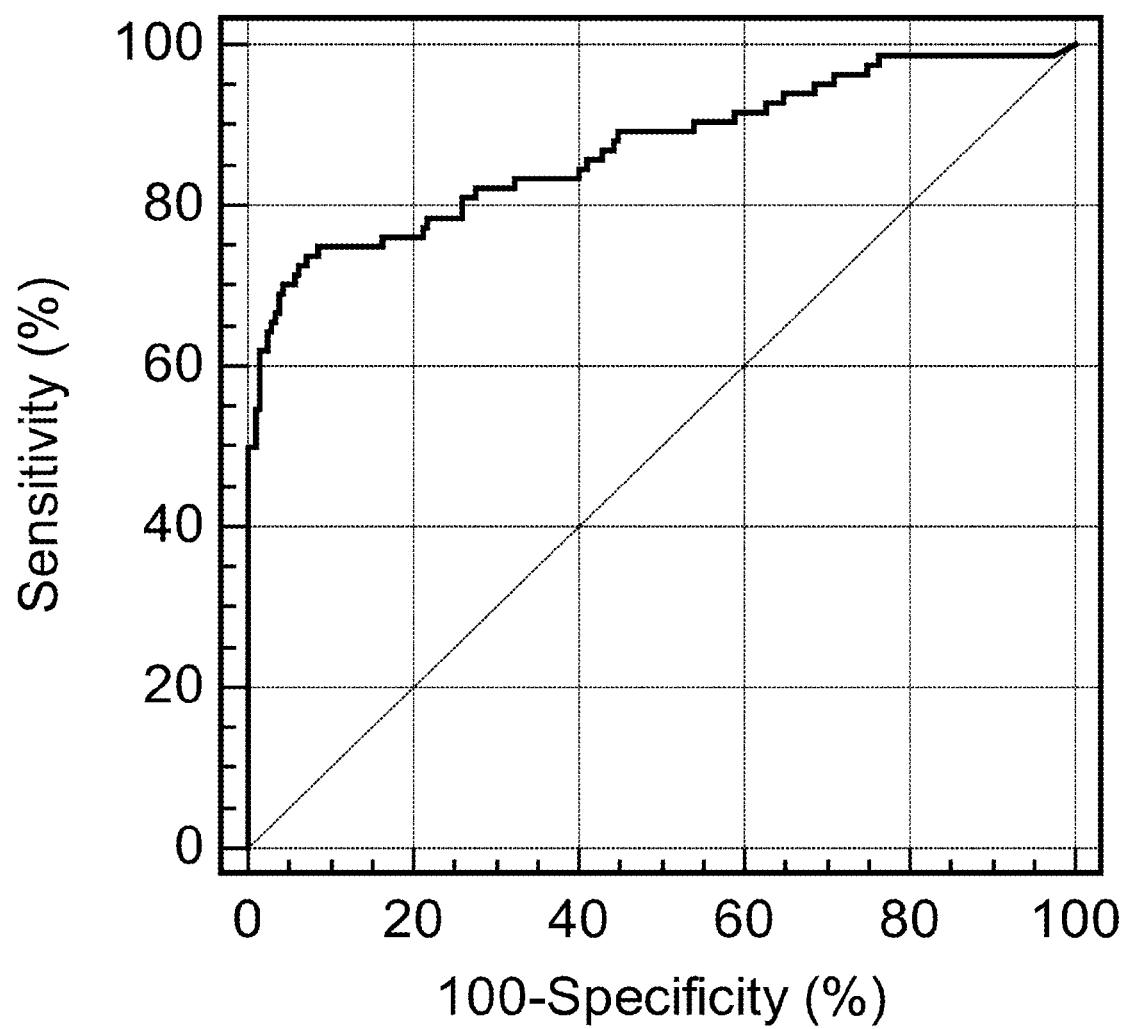
FIG. 7. Receiver-operating characteristic curve for the detection of liver pathologies by plasma ALB mRNA quantification in subjects without elevated plasma ALT.

ROC curve analysis was performed for this subgroup (FIG. 7). The AUC suggested that the diagnostic efficacy of using plasma ALB mRNA as an indicator of liver pathologies was 87%. By using 835 copies/mL of plasma ALB mRNA as a cutoff, the sensitivity and specificity for detecting any one of the assessed liver pathologies were 74% and 93% respectively.

This subgroup analysis further affirms that plasma ALB mRNA analysis is a sensitive marker for the detection of liver pathologies even among individuals with normal liver function test, such as normal plasma ALT level.

Elevated Plasma ALB mRNA as a Predictor of Future Adverse Outcome

The 29 LT recipients who participated in the genotyping study described above were further investigated. Besides genotyping, plasma ALB mRNA concentration was measured by real-time quantitative PCR as described above. Plasma ALT level was also assessed on the same occasion. All of the patients was not known to have developed post-LT HCC at the time of study recruitment, unlike the subjects described in Cheung et al., *Transplantation* 2008; 85:81-7. The participants were monitored for any adverse outcomes that required medical attention or hospital admission for up to 125 weeks. Five participants did not return for follow-up at the Prince of Wales Hospital, Hong Kong, and were excluded from this part of the study. Of the remaining 24 participants, nine developed an adverse outcome other than HCC on a subsequent date as shown in Table 6. Seven of these nine individuals showed elevated plasma ALB mRNA (>835 copies/mL) concentration that predated the development of medical complication. Only three of these subjects had an elevated plasma ALT level at the time of blood taking. These data indicate that elevated plasma ALB mRNA concentration is an early predictor of liver-related complications in post-LT recipients with better performance than plasma ALT. These data indicate that liver-related complications other than HCC can also be predicted by an elevated ALB mRNA level. Among the 15 participants who had not developed liver-related complications, only one person (case 14 in Table 6) had a plasma ALB mRNA level>835 copies/mL. The proportion of subjects with elevated plasma ALB mRNA among those with and without the development of liver-related complications was statistically significantly different (P<0.001, Fisher Exact test). These data indicate that elevated ALB mRNA level is a relatively specific early sign and predictor of liver diseases. The extent of plasma ALB mRNA can be indicative of the severity of the liver complication, i.e., with prognostic value.

Figure 8:
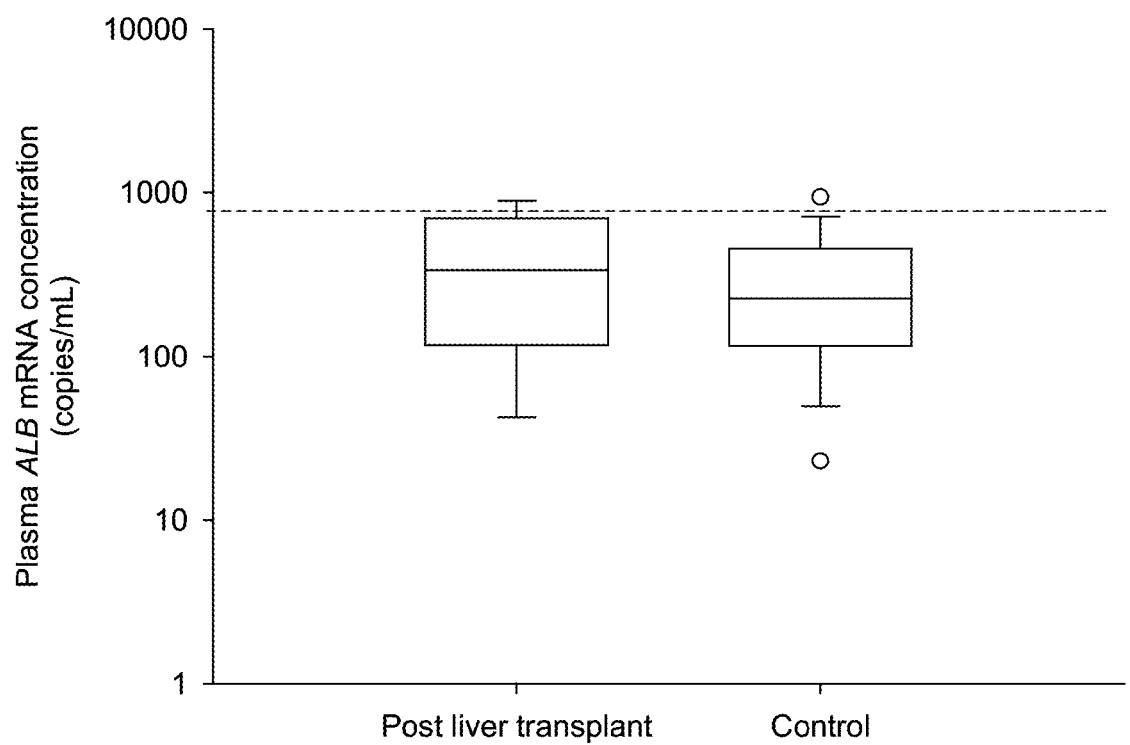
FIG. 8. Box plot of plasma ALB mRNA concentrations in healthy controls and post-liver transplant recipients without elevated plasma ALT. The upper and lower limits of the boxes and the lines across the boxes indicate the $75^{th}$ and $25^{th}$ percentiles and the median, respectively. The whisker caps indicate the $90^{th}$ and $10^{th}$ percentiles. Outliers are illustrated as open circles. The dashed line indicates the cutoff for detecting liver pathologies (835 copies/mL) as used in FIGS. 1 and 6.

Plasma ALB mRNA Concentration in Individuals Who have Fully Recovered from Prior Liver Diseases Resumption of ALB mRNA to normal levels after a liver complication indicates restoration of normal liver function. All of the LT recipients required LT due to conditions that led to severe compromise of their liver function. Thus, they were treated by LT where the original diseased liver was replaced by a healthy liver. For those who did not subsequently develop any liver-related complications in the post-LT period (Table 6), it was interesting to note that the plasma ALB mRNA concentrations were comparable to the healthy controls shown in FIGS. 1 and 6 with no statistically significant difference (P=0.686, Mann-Whitney test) (FIG. 8). These data indicate that despite previous liver insults, after receiving a liver with normal liver function as indicated by the normal plasma ALT and lack of related signs and symptoms, the plasma ALB mRNA concentration reverts to that of normal levels. Similarly, it is expected that for individuals who recovered from liver injuries as indicated by a normal liver function test and lack of related signs and symptoms but did not receive LT as the treatment, the plasma ALB mRNA concentration should normalize. Thus, if plasma ALB mRNA concentration increases at a later stage after recovery, it would be indicative of the development of recurrence or another liver disease.

III. Discussion

There is much excitement over the possibility of developing blood-based tools for disease diagnosis and management through the analysis of circulating nucleic acids (Chan et al. *Ann Clin Biochem* 2003; 40:122-30; Anker et al., *Int J Cancer* 2003; 103:149-52; Lo et al., *Nat Rev Genet* 2007; 8:71-7; Lo et al., *Lancet* 1998; 351:1329-30; Lo et al., *Clin Chem* 2000; 46:319-23). The detection of circulating RNA offers certain advantages over that for DNA (Lambrechts et al., *Ann Oncol* 1998; 9:1269-76). As the expression profile between cell types and diseases are different, tissue- or disease-specific transcripts could be exploited as markers for disease assessment. If a RNA transcript that is unique to a particular organ was selected, the RNA approach may be more generally applicable to diseases of that organ and not limited to the fraction of cases harboring specific DNA signatures. Furthermore, if both plasma RNA and DNA were derived from the same cell population, the released RNA would likely be quantitatively more abundant than that for DNA. This is because multiple copies of a RNA transcript could be present in each cell depending on its expression level, while each cell only contains one diploid genome-equivalent of DNA. Indeed, some cancer researchers reported that a greater proportion of cancer cases were positive for the investigated plasma RNA than DNA markers (Anker et al., *Int J Cancer* 2003; 103:149-52).

An increasing amount of evidence suggests that liberation of cell-free nucleic acids into plasma from organs or compartments is likely to be due to cell death (Jahr et al., *Cancer Res* 2001; 61:1659-65; Fournie et al., *Cancer Lett* 1995; 91:221-7; Fournie et al., *Gerontology* 1993; 39:215-21). The liver being one of the largest organs of the body, we suspect that liver expressed RNA, such as ALB, should be detectable in the peripheral circulation as a result of cell death associated with normal cell turnover and/or pathological damage. Indeed, studies have reported the presence of circulating ALB mRNA but with varying degrees of success (Cheung et al., *Transplantation* 2008; 85:81-7). Some researchers suggested that the blood ALB mRNA originated from malignant or non-malignant hepatocytes that have entered into the peripheral circulation (Hillaire et al., *Gastroenterology* 1994; 106:239-42; Kar et al., *Hepatology* 1995; 21:403-7). However, Muller et al. (*Hepatology* 1997; 25:896-9) reported that peripheral mononuclear cells can be induced to express ALB mRNA. Indeed, previous reports indicated that certain supposedly organ-specific transcripts detectable in the circulation may in fact be derived from other cell populations, such as hematopoietic cells (Chan et al., *Clin Chem* 2007; 53:1874-6; Heung et al., *PLoS One* 2009; 4:e5858) due to illegitimate gene transcription (Lambrechts et al., *Ann Oncol* 1998; 9:1269-76; Chelly et al., *Proc Natl Acad Sci USA* 1989; 86:2617-21).

Thus, in this study, the inventors first aimed to confirm if ALB mRNA detectable in human plasma and whole blood were derived from and specific to the liver. Donor and recipient pairs of LT or BMT were studied who were genotypically different for an ALB coding SNP and determined the RNA-SNP genotypes in plasma and whole blood. The data demonstrated that the ALB mRNA detected in plasma but not whole blood was liver-specific. The data also indicated that ALB mRNA expressed by hematopoietic cells could contribute to the pool of ALB mRNA detected in whole blood. These findings call for caution in the interpretation of the previously reported data on ALB mRNA detection in whole blood. Plasma is preferred over whole blood for future studies on ALB mRNA as a biomarker for liver diseases. To minimize the chance of residual blood cells contaminating the ALB mRNA molecules in plasma, plasma should be prepared by two centrifugation steps as previously reported.

The inventors then developed a one-step RT-qPCR assay for plasma ALB mRNA quantification. The detection rate for plasma ALB mRNA in our study was 98.1%. Using two-step RT-qPCR, a recent study investigated the role of plasma ALB mRNA detection for prediction of HCC recurrence in liver transplant recipients reported a detection rate of 82% (Cheung et al., *Transplantation* 2008; 85:81-7). In the discussion section of their report, Cheung et al. stated that they believed the positive detection of plasma ALB mRNA indicated the presence of circulating HCC cells while LT recipients negative for plasma ALB mRNA suggested the absence of HCC cells in the circulation. Data from the present study, however, showed that plasma ALB mRNA is detectable in plasma of almost all subjects, including healthy controls. These data indicate that circulating HCC cells are not the sole source of plasma ALB mRNA if at all. Thus, plasma ALB mRNA is more likely to be released into plasma due to any liver cell death and is useful for the detection of a range of liver diseases not limited to post-LT HCC. It is believed that the improvement by the present inventors in the detection rate for plasma ALB mRNA may be related to the analytical sensitivity of the one-step RT-qPCR protocol and their targeting of the more 5' end of the ALB gene. The inventors have previously reported that circulating mRNA in plasma may not be intact full-length transcripts and showed a 5' predominance (Wong et al., *Clin Chem* 2005; 51:1786-95).

It was found that plasma ALB mRNA concentrations were significantly higher than controls in patients with HCC, cirrhosis, and active CHB but not inactive CHB. These data indicate that ALB mRNA is released into plasma as a result of cell death and may correlate with the degree of cell death.

By ROC curve analysis, it was found that plasma ALB mRNA measurement was an attractive means (92.9%) for detecting the presence of liver pathologies. In particular, for the HCC group, alpha-fetoprotein was only elevated in 48.6% of the cases while the majority (91.4%) showed elevated ALB mRNA concentrations.

Albeit its diagnostic sensitivity, plasma ALB mRNA is not specific towards liver pathologies of any particular etiology. However, plasma ALB mRNA concentration bore some correlation with serum ALT activity-concentration. Plasma ALB mRNA was also found to be elevated in patients with liver disease but normal ALT levels (FIG. 3). These observations indicate that plasma ALB mRNA is a sensitive marker for the detection of early stage chronic liver disease where ALT activity-concentration is often within reference limits.

In summary, experimental data by the present inventors revealed that plasma but not whole blood ALB mRNA was derived from and specific to the liver. Elevation of plasma ALB mRNA concentrations was observed for a range of liver pathologies and further studies are required to investigate its clinical utility in the assessment or management of such diseases.

Example 2

Sensitive Detection of Post-Liver Transplantation Complications by Plasma Albumin mRNA Monitoring In this study, the present inventors showed that significantly elevated concentrations of plasma ALB mRNA were associated with chronic hepatitis, liver cirrhosis and hepatocellular carcinoma (HCC). Their data revealed that plasma ALB mRNA was more sensitive than plasma alanine transaminase (ALT) activity for the detection of liver pathologies. Long term monitoring of liver function and the early detection of hepatic insults are important aspects of the continual care of patients with various liver pathologies, including the post-liver transplantation recipients. Hence, this study was aimed to investigate whether plasma ALB mRNA measurements offered any value in the care of patients known previously to have suffered from liver pathologies, using recipients of liver transplantation as an example.

I. Materials and Methods

Participants

From June 2006 to July 2009, 24 patients were recruited who previously underwent liver transplantation at the Department of Surgery, the Prince of Wales Hospital, Hong Kong. The post-liver transplantation recipients were typically seen at the liver transplantation clinic every three to six months, or more often if clinically indicated. During each visit, physical, biochemical and serological examinations were performed. The serial analysis of plasma ALB mRNA in this study involved a maximum of 7 collections of 6 mL of peripheral blood from a forearm vein within the 3-year time period. Ethical approval was obtained from the institutional review board and informed consent was obtained from each recipient.

Sample Collection and Processing

The methods of sample collection and processing were as has been described (Chan et al., *Clin. Chem.* 2010; 56:82-9). In brief, the blood specimens collected into EDTA-containing tubes were immediately kept at 4° C. and processed within 4 h. Plasma was harvested by a double-centrifugation protocol (Chiu et al., *Clin. Chem.* 2001; 47:1607-13)). Plasma RNA was extracted by a protocol involving the use of RNeasy Mini Kit (Qiagen, Valencia, Calif.) with TRIzol LS reagent (Invitrogen, Carlsbad, Calif.) (Heung et al., *Prenat. Diagn.* 2009; 29:277-9). Total RNA was eluted in 50 μL of RNase-free water and treated with Amplification Grade Deoxyribonuclease I (Invitrogen) according to the manufacturer's instructions and then stored at −80° C. until use.

Quantification of ALB mRNA Transcript in Plasma

One-step reverse-transcription quantitative real-time polymerase chain reaction (RT-qPCR) was used to measure the plasma ALB mRNA concentrations. Briefly, the intron-spanning assay for ALB mRNA quantification was designed to amplify a 78-bp ALB amplicon across exon 1 and exon 2 at the 5' region. The reaction was set up using the EZ rTth RNA PCR reagent set (Applied Biosystems, Foster City, Calif.) in a reaction volume of 25 μL. Calibration curves for absolute ALB mRNA quantification were prepared by subjecting serial dilutions of High Performance Liquid Chromatography-purified single-stranded synthetic DNA oligonucleotides (Sigma-Proligo, Singapore) specifying the targeted ALB amplicon. The lower limit of detection of this assay was 1 copy per reaction with a range of linearity up to $10^6$ copies per reaction. Each sample was analyzed in duplicate, and the corresponding calibration curve was run in parallel with each analysis. The amplification of ALB mRNA was monitored by an ABI Prism 7900 Sequence Detector (Applied Biosystems) and the Sequence Detection Software version 2.2 (Applied Biosystems). Absolute concentrations of ALB mRNA in plasma were expressed as copies/mL.

Assessment of Liver Function

Plasma analysis for albumin, total bilirubin, alkaline phosphatase (ALP), alanine transaminase (ALT) and alpha-fetoprotein was performed by the Chemical Pathology laboratory of the pH, using the DPE Modular Analytics system (Roche Diagnostics, Basel, Switzerland).

Statistical Analysis

Statistical analyses were performed using the SigmaStat for Windows Version 3.5 software (Systat Software Inc., Chicago, Ill.). Continuous variables were expressed as median and range. Plasma ALB mRNA concentrations and other parameters were compared between groups by the Kruskal-Wallis H test and Mann-Whitney U test as appropriate. Correlations between plasma ALB mRNA concentrations and other parameters were determined by the Spearman's rank correlation. A p-value of less than 0.05 was considered as statistically significant and all probabilities were two tailed.

II. Results

A total of 24 liver recipients, 20 males and 4 females, who had at least 3 blood collections for plasma ALB mRNA measurement during the study period, were studied. The liver transplantations were performed at the PWH between 1991 and 2004. Nine were living donor liver transplantations while 15 were deceased donor liver transplantations. The indications for liver transplantations included HCC (12 cases), cirrhosis (7 cases), hepatic failure (3 cases), fulminant hepatitis B (1 case) and alcoholic cirrhosis (1 case).

In this study, the 24 recipients were divided into two groups according to whether they developed liver-associated clinical sequelae during the study period. Fourteen recipients (12 males and 2 females) had unremarkable course as reflected by their stable clinical condition and biochemical liver function test profile were classified as the 'Stable' group. On the other hand, 10 recipients (8 males and 2 females) who had evidence of single or multiple episodes of liver-associated complications requiring hospitalization or surgical management during the study period were classified as the 'Unstable' group. None of the 24 recipients had HCC recurrence during the study period.

Initial Analyses at the Time of Study Enrollment

At enrollment, the median age of the 24 recipients was 56.2 years old (range, 17-69) and there was no statistically significant difference in the median ages between the Stable and Unstable groups (Mann-Whitney U test, P=0.254).

All 14 recipients in the Stable group were deemed to be clinically stable at the time of enrollment based on an assessment by a hepatologist and the satisfactory biochemical liver function test profile. For the stable group, the median plasma values of albumin, bilirubin, ALP and ALT levels were 44 g/L (40-49), 15 μmol/L (7-38), 82 U/L (59-290) and 32 U/L (10-69), respectively.

Nine of the ten recipients in the Unstable group were clinically stable at the time of enrollment into the study. The one exception, recipient No. U07, was diagnosed with recurrence of alcoholic cirrhosis and mild chronic rejection at the time of enrollment. The median plasma albumin, bilirubin, ALP and ALT concentrations of the Unstable group were 44 g/L (38-45), 19 μmol/L (10-31), 169 U/L (73-379) and 53 U/L (24-155), respectively. There was no statistically significant difference in the plasma concentrations of albumin (P=0.341) and bilirubin (P=0.538) between the two groups. However, the plasma ALP (P=0.015) and ALT (P=0.035) concentrations of the Unstable group were statistically significantly higher than the Stable group.

Figure 9:
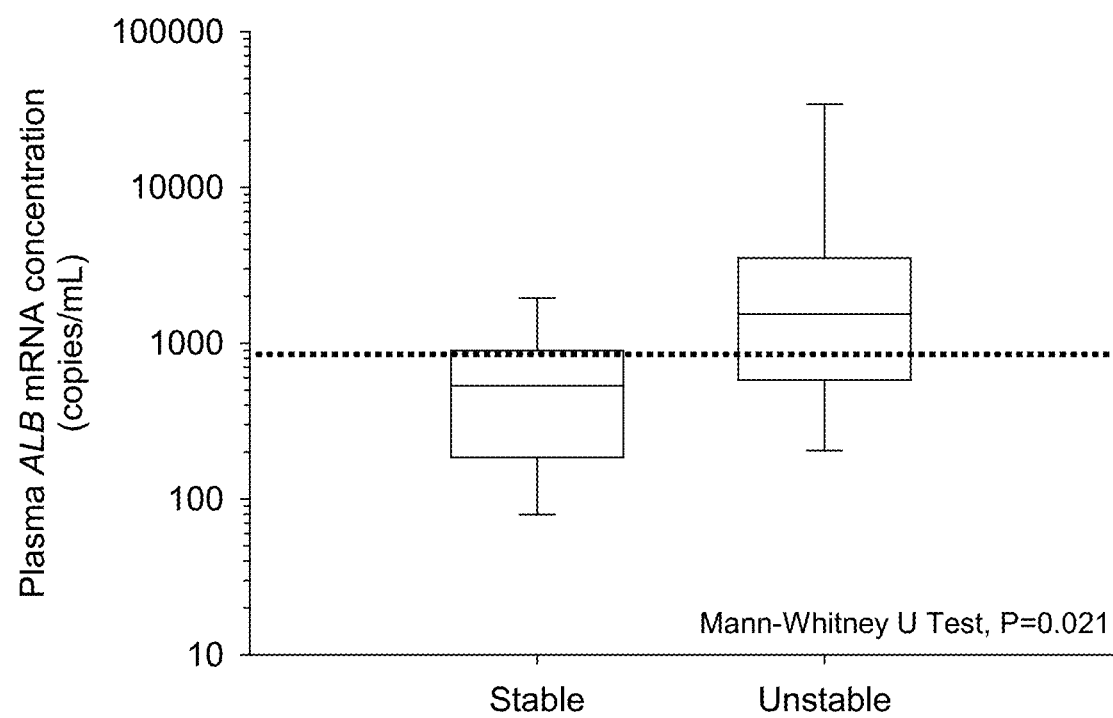
FIG. 9. Box plot showing the plasma ALB mRNA concentrations of the Stable and Unstable groups at the time of enrollment. The upper and lower limits of the boxes and the lines across the boxes indicate the $75^{th}$ and $25^{th}$ percentiles and the median, respectively. The whisker caps indicate the $90^{th}$ and $10^{th}$ percentiles. Outliers are illustrated as open circles. The plasma ALB mRNA cutoff level of 835 copies/mL is represented by the dotted line.

The plasma ALB mRNA concentrations of the two groups at the time of enrollment were shown in FIG. 9. The median plasma ALB mRNA concentration of the Stable group was 533 copies/mL (69-2,399) while that of the Unstable group was 1,540 copies/mL (203-37,524) (P=0.021, Mann-Whitney U test). In their previous study (Chan et al., *Clin. Chem.* 2010; 56:82-9), using receiver-operating characteristic curve analysis, the inventors identified 835 copies/mL as a sensitive and specific cutoff for distinguishing healthy controls from patients with liver pathologies. Adopting the same cutoff for this study, the inventors found that 21% (3/14) and 70% (7/10) of those in the Stable and Unstable groups, respectively, had elevated plasma ALB mRNA concentrations. The proportion of cases with elevated plasma ALB mRNA concentrations among the two groups was statistically significantly different (Chi-square P<0.0001). The inventors further studied the relationship between plasma ALB mRNA concentration and the biochemical liver function test parameters of the 24 recipients. Plasma ALB mRNA concentration was significantly correlated with the plasma concentrations of ALP (Spearman correlation, $r^2$=0.71, P<0.0351) and ALT ($r^2$=0.45, P=0.03), but not with albumin ($r^2$=−0.16, P=0.46) or bilirubin ($r^2$=0.15, P=0.5).

Serial Monitoring of Plasma ALB mRNA

Figure 10A:
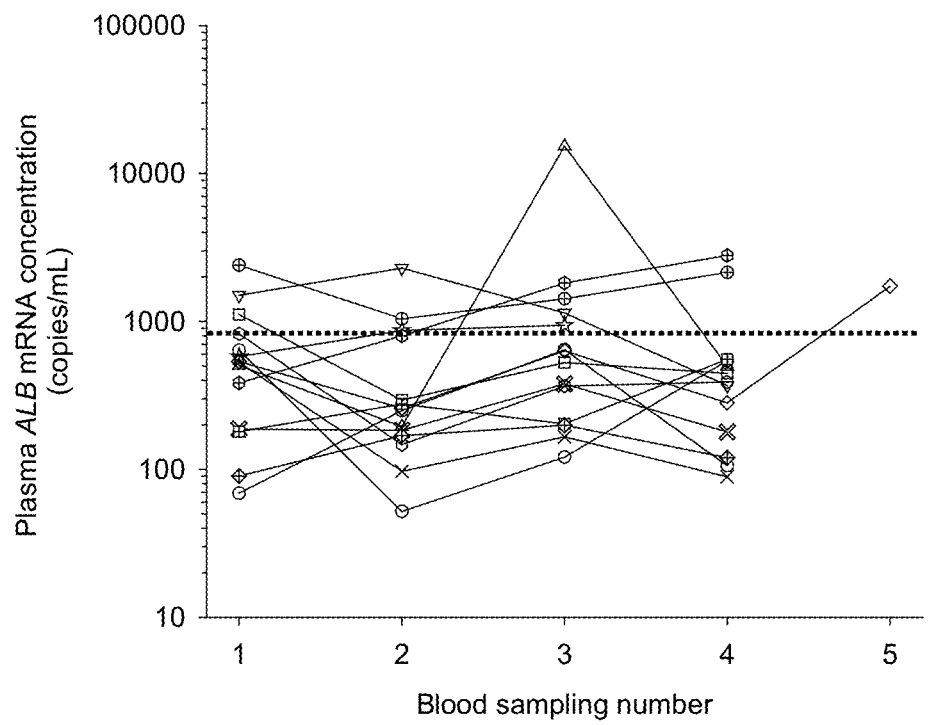
FIGS. 10A and 10B. Plasma ALB mRNA concentrations for blood samples taken over the entire duration of the study for recipients in (FIG. 10A) the Stable group and (FIG. 10B) the Unstable groups. Plasma ALB mRNA levels of stable and unstable recipients are represented by open symbols with dashed lines and closed symbols with solid lines respectively. The plasma ALB mRNA cutoff level of 835 copies/mL is represented by the dotted line.

The clinical course of the 24 recipients were followed for a median duration of 110 weeks. The overall study period of the Stable group, 112 weeks (87-160), was comparable with that of the Unstable group, 107 weeks (69-159), without any statistically significant difference (P=0.412). During the study period, 105 blood specimens (56 from the Stable group and 49 from the Unstable group) were collected for plasma ALB mRNA analysis and all had detectable plasma ALB mRNA Post-Liver Transplantation Recipients with Stable Clinical Course Twelve of the 14 recipients (86%) in the Stable group had unremarkable clinical course throughout the study period. The median values of the albumin, bilirubin, ALP and ALT plasma concentrations of the Stable group for all measurements taken during the study were 44 g/L (35-49), 15 µmol/L (5-38), 85 U/L (59-290) and 28 U/L (10-158), respectively. Consistent with the first blood sample taken at enrollment, the median concentration of plasma ALB mRNA of the Stable group was 418 copies/mL (52-15,320). FIG. 10A is a plot of all plasma ALB mRNA measurements taken from the Stable group. Only 25% (14/56) of the plasma ALB mRNA measurements were above 835 copies/mL. When all plasma ALB mRNA measurements from the Stable group were grouped, the $5^{th}$ and $95^{th}$ percentile values were 90 copies/mL and 2,400 copies/mL, respectively. The biochemical liver function test profile remained unremarkable on all occasions for these 12 recipients.

Of the 14 stable recipients, 2 (14%) had an occasional rise in the biochemical liver function test parameters which returned promptly to within the normal range without intervention. The plasma ALB mRNA concentrations from the two recipients measured during those occasions were 15,320 and 2,399 copies/mL. Yet, the levels returned to 497 and 1,044 copies/mL, respectively, upon the subsequent visit. The correlation analysis demonstrated that the plasma ALB mRNA concentrations measured from the 14 stable recipients during the study period were not significantly correlated to the plasma concentrations of ALP ($r^2$=0.41, P=0.002), but not for albumin ($r^2$=−0.06, P=0.68), bilirubin ($r^2$=−0.19, P=0.16), ALT ($r^2$=0.19, P=0.16).

Post-Liver Transplantation Recipients with Unstable Clinical Course

Figure 10B:
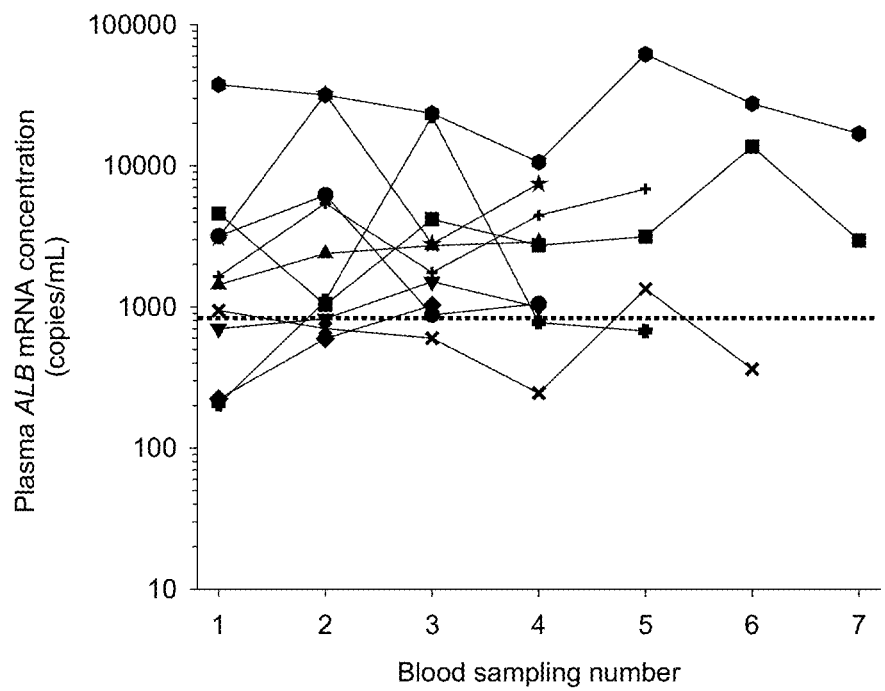
Figure 11A:
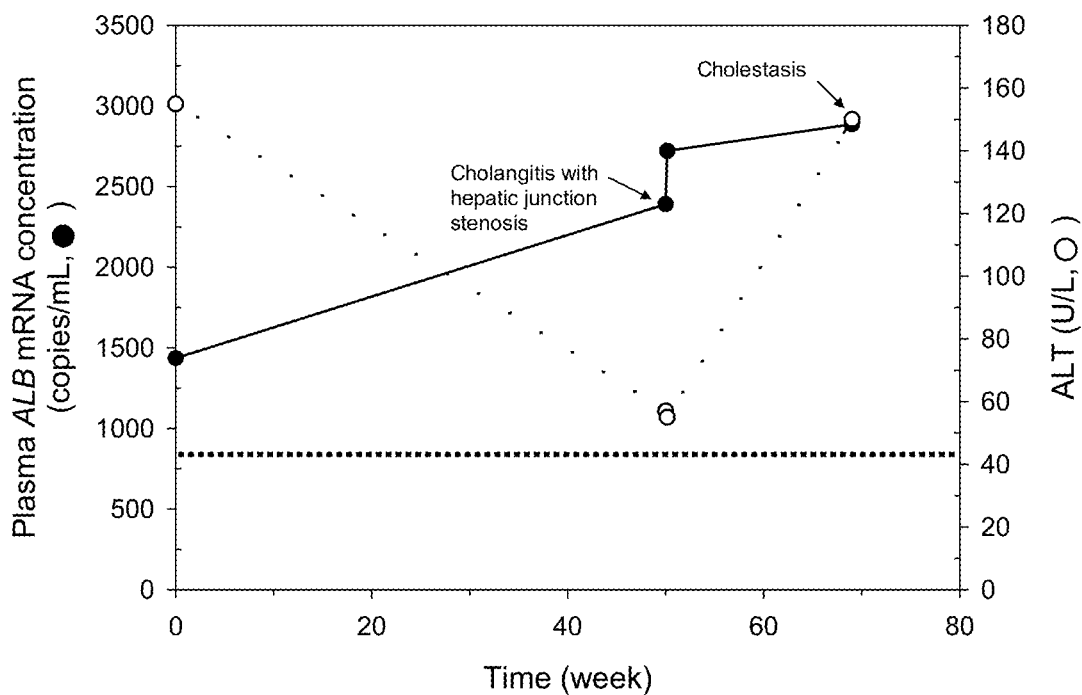
FIGS. 11A to 11F. Serial measurements of plasma ALB mRNA and ALT among recipients with acute liver complications.
Figure 11B:
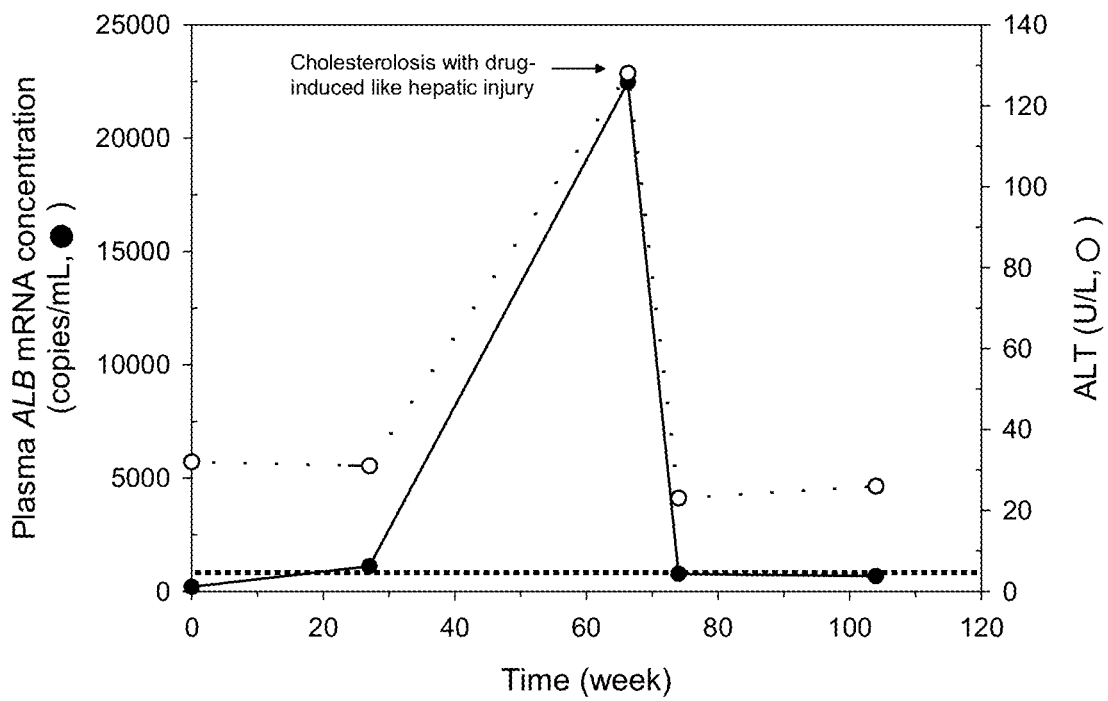
Figure 11C:
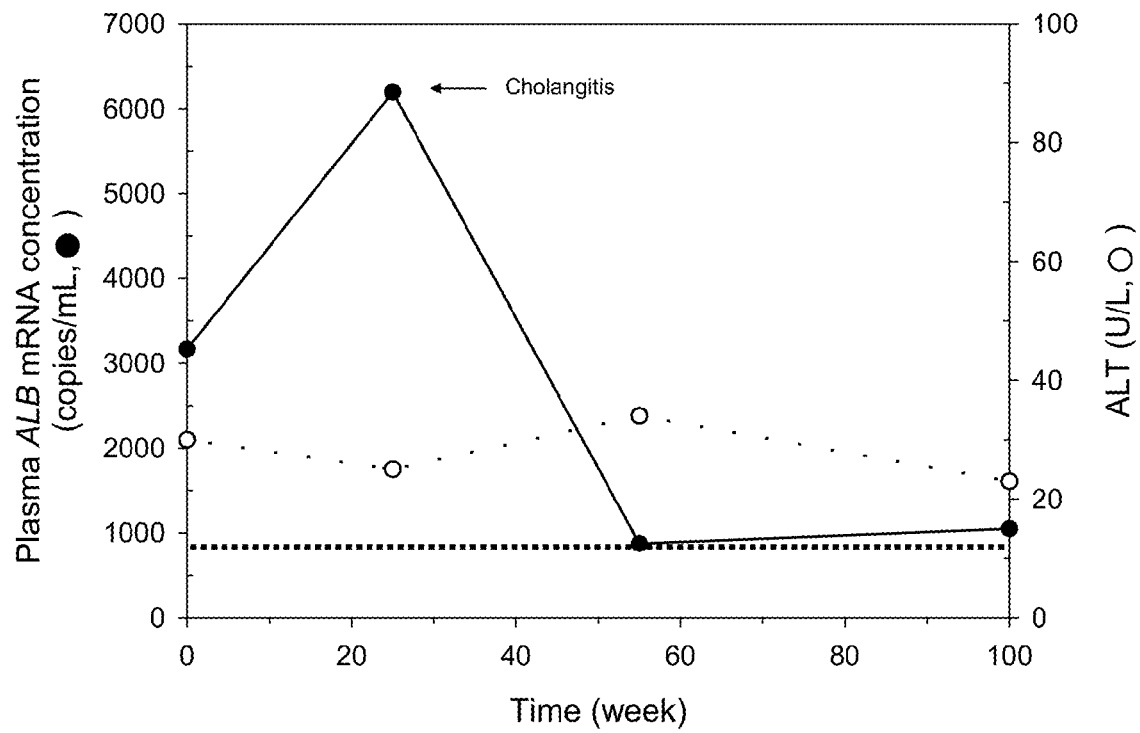
Figure 11D:
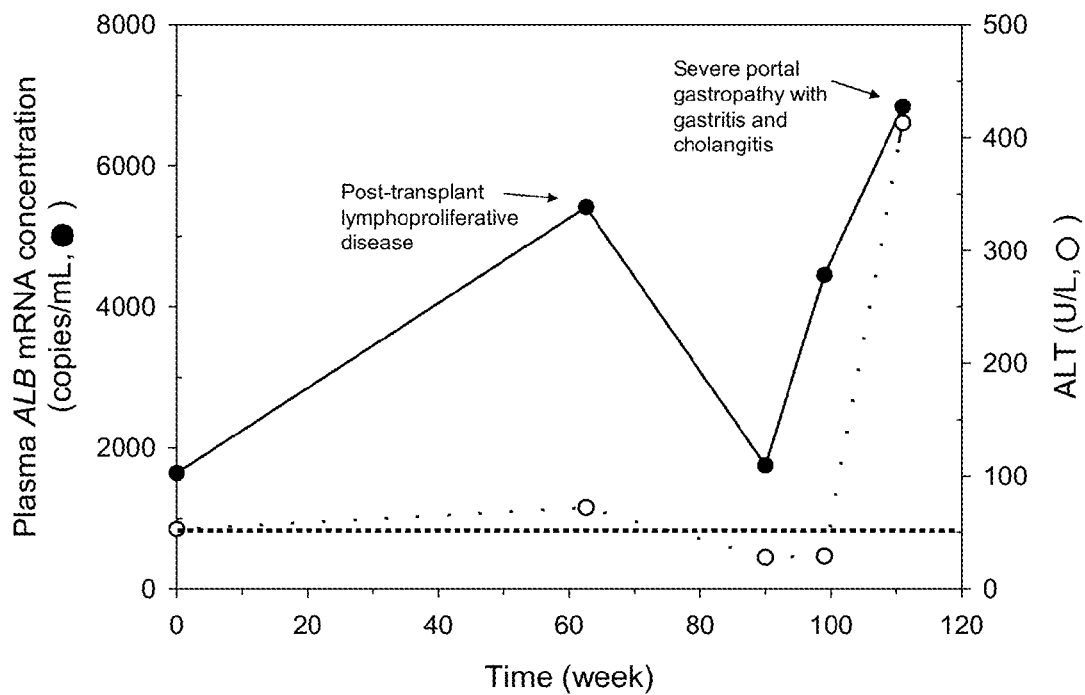
Figure 11E:
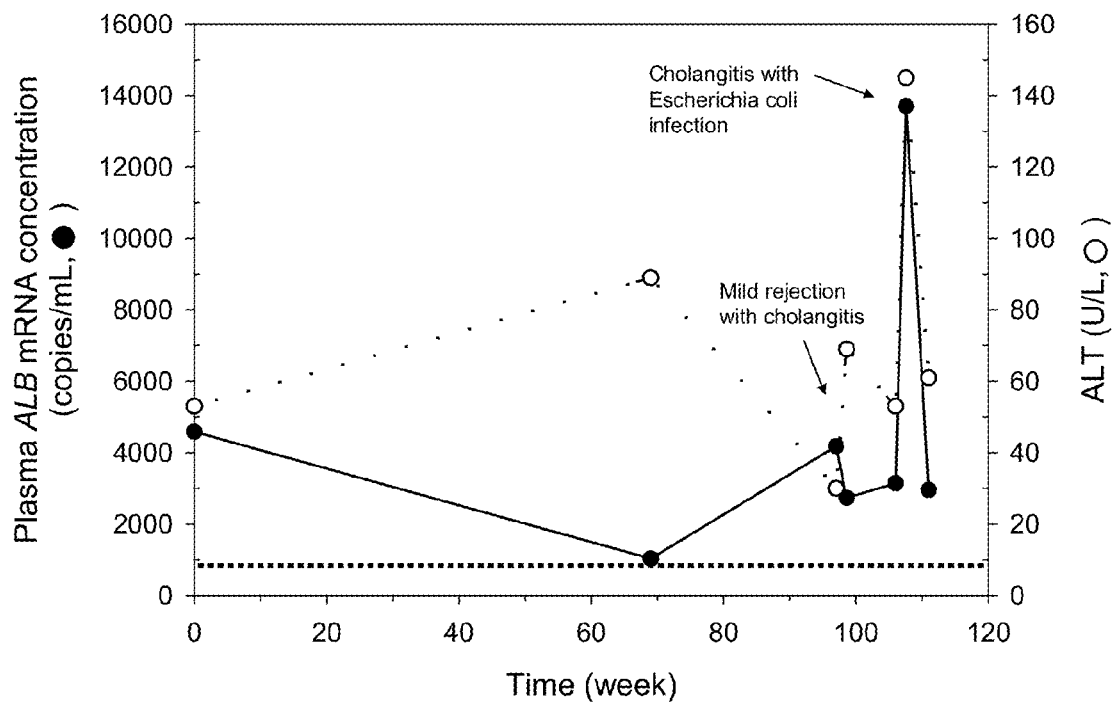
Figure 11F:
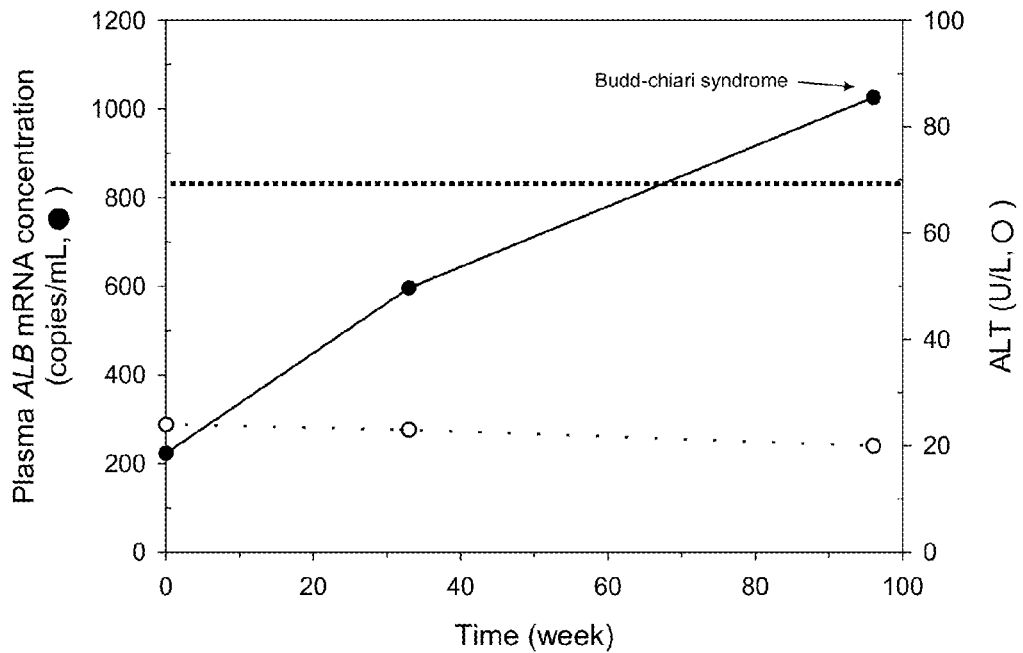
Figure 12A:
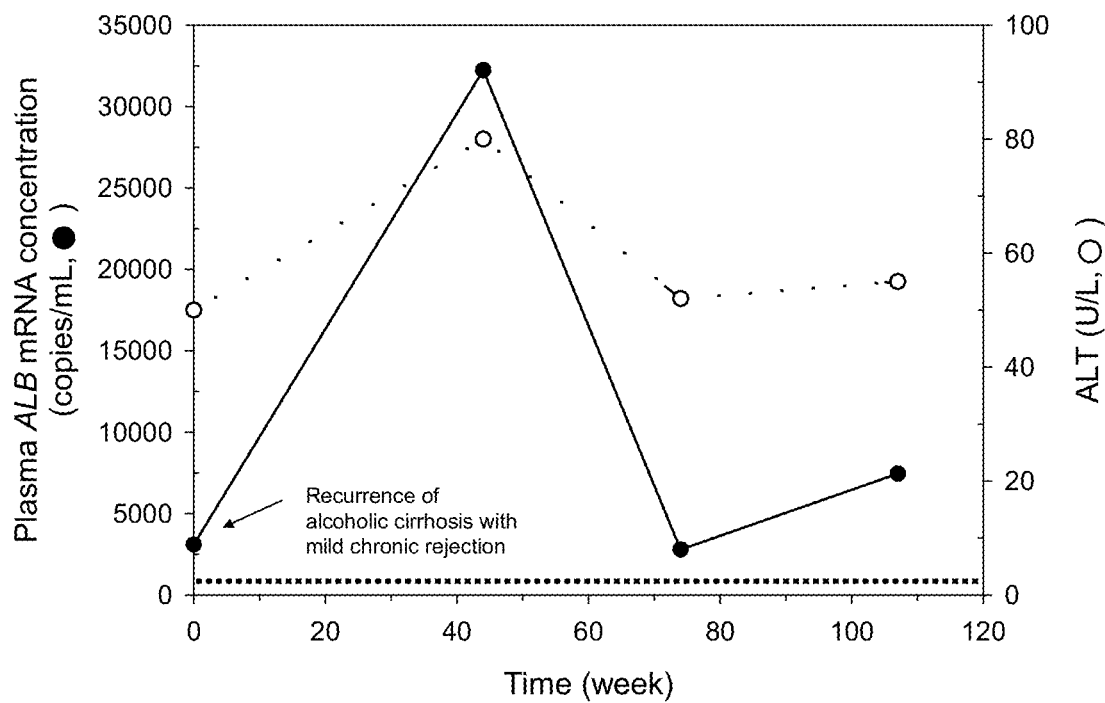
FIGS. 12A to 12D. Serial measurements of plasma ALB mRNA and ALT among recipients with chronic liver complications.
Figure 12B:
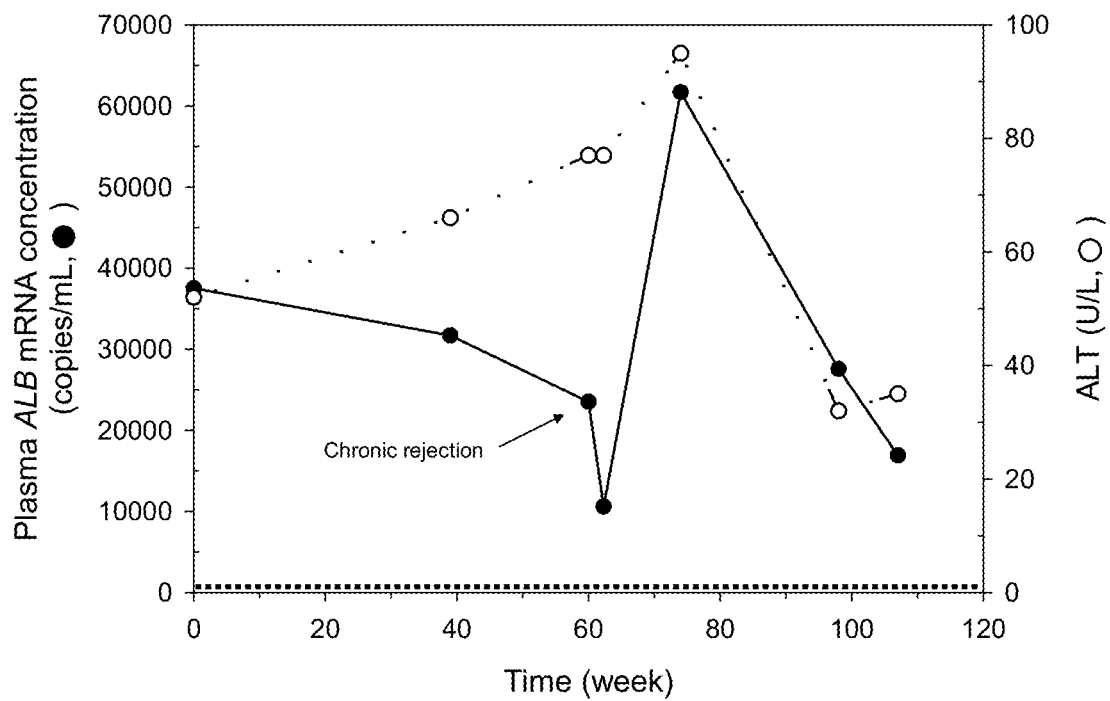
Figure 12C:
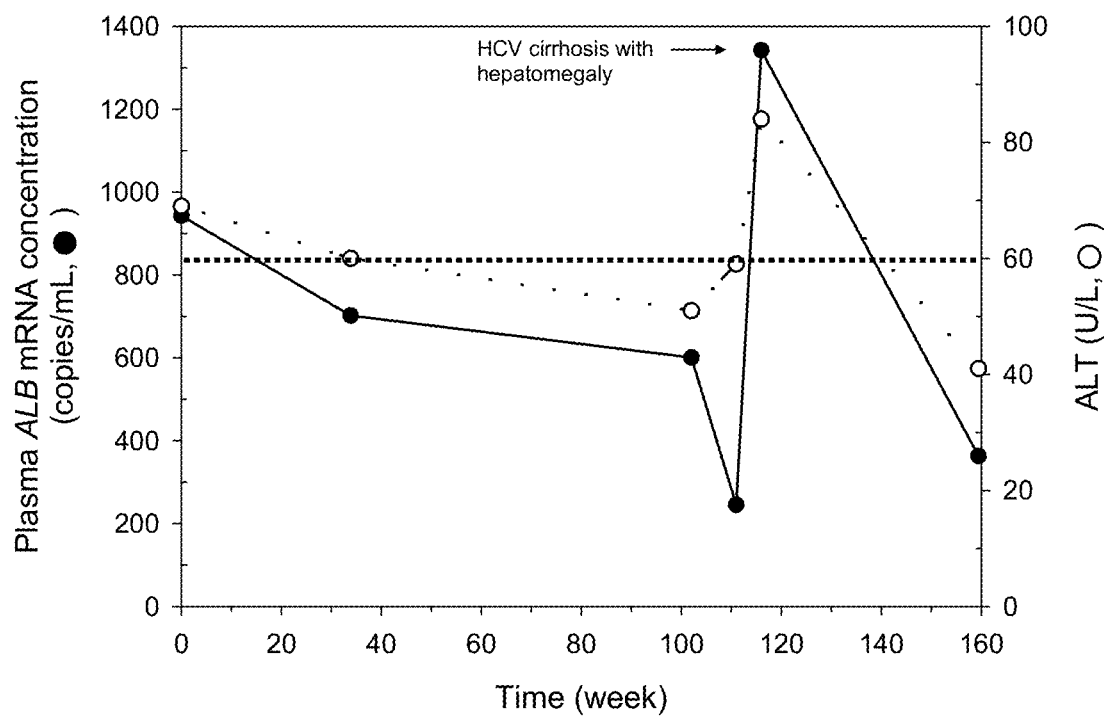
Figure 12D:
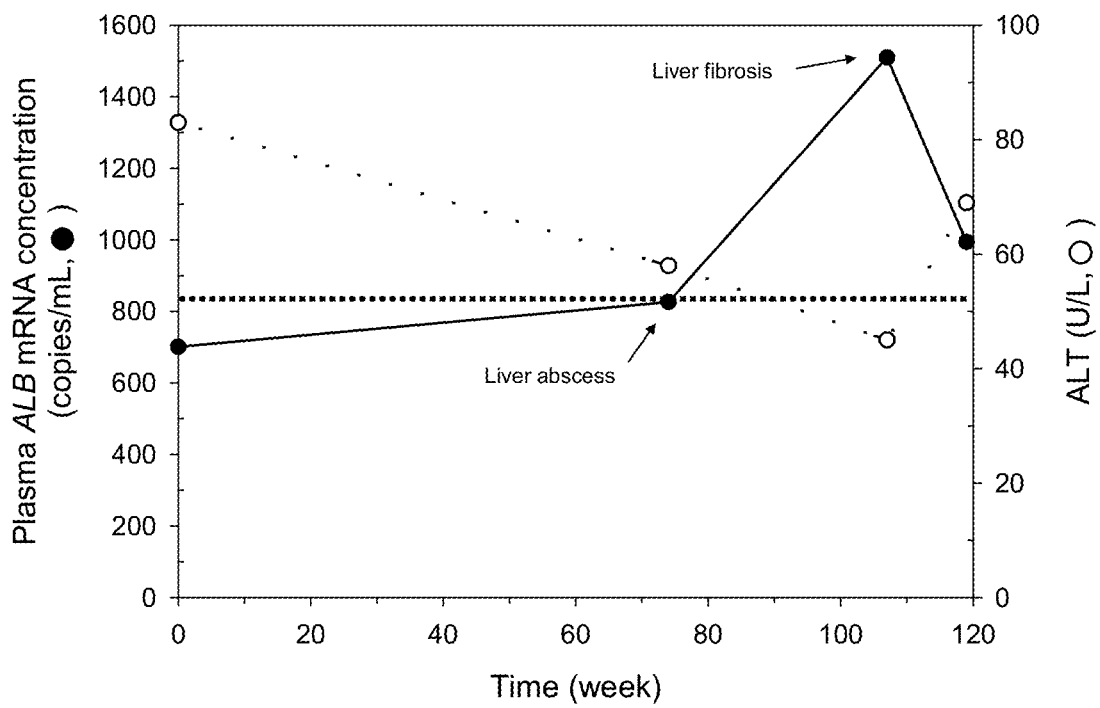

The 10 recipients in the Unstable group had at least one episode of liver-associated complication during the study period. Table 7 lists the liver-associated complications developed among the recipients of the Unstable group during the study period. Grouping all the measurements taken throughout the study period, the median plasma albumin, bilirubin, ALP and ALT concentrations among recipients of the Unstable group were 40 g/L (16-46), 23 µmol/L (5-250), 150 U/L (46-601) and 50 U/L (20-413), respectively. The median plasma ALB mRNA level of the Unstable group was 2,721 copies/mL (203-61,694), which was 6.5-fold higher than that of the Stable group (418 copies/mL). In contrast to the persistently low concentrations of plasma ALB mRNA observed among the stable recipients, highly fluctuant or even persistently elevated concentrations of plasma ALB mRNA could be observed in the unstable recipients, as illustrated in FIG. 10B. 78% (38/49) of the plasma ALB mRNA measurements from the Unstable group were above 835 copies/mL. The proportion of measurements with elevated plasma ALB mRNA concentrations in the Stable and Unstable groups was statistically significantly different (Chi-square P<0.0001).

For the 10 recipients in the Unstable group, six developed acute liver complications (Cases U01 to U06) and four had chronic liver complications (Cases U07 to U10). The serial measurements of the plasma ALB mRNA concentrations and the ALT activity-concentrations for the acute and chronic groups were plotted in FIGS. 11A-11F and 12A-12D, respectively.

Unstable Recipients with Acute Liver-Associated Complications

The time of diagnosis of each episode of liver-associated complications is marked in the plots within FIGS. 11A-11F and 12A-12D. Among the six recipients with documented acute liver-associated complications, elevation in plasma ALB mRNA concentrations (beyond the cutoff value of 835 copies/mL) predated the time the diagnosis of the complication was made in four cases (FIGS. 11A-11F). In total, nine episodes of complications were documented for cases U01 to U06. The plasma ALB mRNA concentrations were elevated in all episodes of complications at the time when the diagnoses were made. In contrast, the plasma ALT activity was only elevated (>58 U/L) in four of the nine episodes.

Unstable Recipients with Chronic Liver-Associated Complications

Four recipients in the Unstable group had a total of five episodes of liver-associated complications that were chronic in nature. The plasma ALB mRNA concentrations were elevated at the time of diagnosis except when case U10 was found to have a liver abscess (FIGS. 12A-12D). Plasma ALT activity was elevated at the time of diagnosis of three of the episodes.

III. Discussion

In this study, the present inventors further confirmed their previous data that plasma ALB mRNA is a sensitive marker for liver pathologies. In this study, post-liver transplantation recipients were used as an example. Twenty-three of the 24 recruited recipients were clinically stable, had normal biochemical liver function test profile and were clinically judged to be free from medical or surgical complications at the time of enrollment. During serial monitoring, it was found that the plasma ALB mRNA concentrations were elevated at the time when clinical diagnoses of various complications were made. Among the Unstable group, 13 of the 14 documented episodes of complications were associated with elevated ALB mRNA concentrations. In fact, the plasma ALB mRNA concentrations were elevated before the time the diagnosis was made in the majority of the episodes. These data further affirm that plasma ALB mRNA is a sensitive marker with utility in the early diagnosis of liver pathologies. For most acute episodes of complications, the plasma ALT activity-concentrations were not elevated. This observation indicates that plasma ALB mRNA is a more sensitive marker for liver pathologies than ALT.

On the other hand, elevation in plasma ALB mRNA concentration is specific to the occurrence of liver pathologies. Majority of the measurements taken from the Stable group were below the previously established cutoff value for the detection of liver diseases. Two recipients in the Stable group had transiently elevated concentrations of plasma ALB mRNA. These occurrences may be associated with transient liver-associated complications that were not identified clinically.

In summary, elevations in plasma ALB mRNA concentrations allow the sensitive and specific detection of liver pathologies, even at a stage when the recipient was symptom-free, the plasma ALT activity-concentrations were normal and there were no clinical suspicion of complications. Thus, measurement of plasma ALB mRNA concentration serves as a useful approach for the screening of liver pathologies and regular monitoring of persons who may develop liver-associated complications. As the majority of the liver transplantation recipients that were studied in this project had fully recovered from their original liver disease and the transplantation, the observations that the inventors made within this study can be applied to any persons with no prior history of liver disease or had recovered from prior episodes of liver diseases.

Example 3

Elevated Plasma Albumin mRNA Concentration for the Detection of Fatty Liver Disease Fatty liver disease, including nonalcoholic fatty liver disease, is the most common chronic liver disease in affluent countries (Farrell et al., *J Gastroenterol Hepatol* 2007; 22:775-7. It may progress to cirrhosis and liver cancer. Nonalcoholic fatty liver disease is closely associated with metabolic syndrome and central obesity (Wong et al., *Clin Gastroenterol Hepatol* 2006; 4:1154-61).

Ultrasound scan can be used for the diagnosis of fatty liver. However, ultrasound scan is operator dependent, and has limited sensitivity and specificity for the diagnosis of fatty liver. Liver biopsy and histological examination provide the definitive proof of fatty liver and any associated hepatic inflammation or fibrosis, but the biopsy is an invasive procedure and may result in acute complications such as hemorrhage. With advances in technology, it is now possible to use proton magnetic resonance spectroscopy (MRS) as a sensitive and noninvasive technique to measure hepatic triglyceride (IHTG) content, a indicator of fatty liver (Szczepaniak et al., *Am J Physiol Endocrinol Metab* 2005; 288:E462-8). However, MRS imaging is time-consuming, requires specialized imaging equipment and trained expert operator. In this study the inventors examined whether plasma ALB mRNA is elevated in patients with fatty liver when compared with healthy controls.

I. Materials and Methods

MRS was performed on apparently healthy volunteers. The IHTG content was measured. Subjects with IHTG content<5% were deemed to have healthy livers while those with IHTG content>5% were diagnosed with fatty liver disease. In addition, the study also included individuals who were diagnosed to have fatty liver disease by histological examination of a liver biopsy. Peripheral blood was collected from all recruited subjects into EDTA blood tubes. The blood samples were processed by the double centrifugation protocol as described in the earlier examples to obtain plasma. Plasma ALB mRNA concentration was then measured using the RT-qPCR assay described in the earlier examples.

II. Results 136 volunteers were found by MRS to have IHTG content<5% and therefore were recruited as normal controls. 47 individuals were found by MRS to have IHTG content>5% and hence were diagnosed as having fatty liver disease. 35 individuals were diagnosed with fatty liver disease through histological examination of a liver biopsy.

Figure 13:
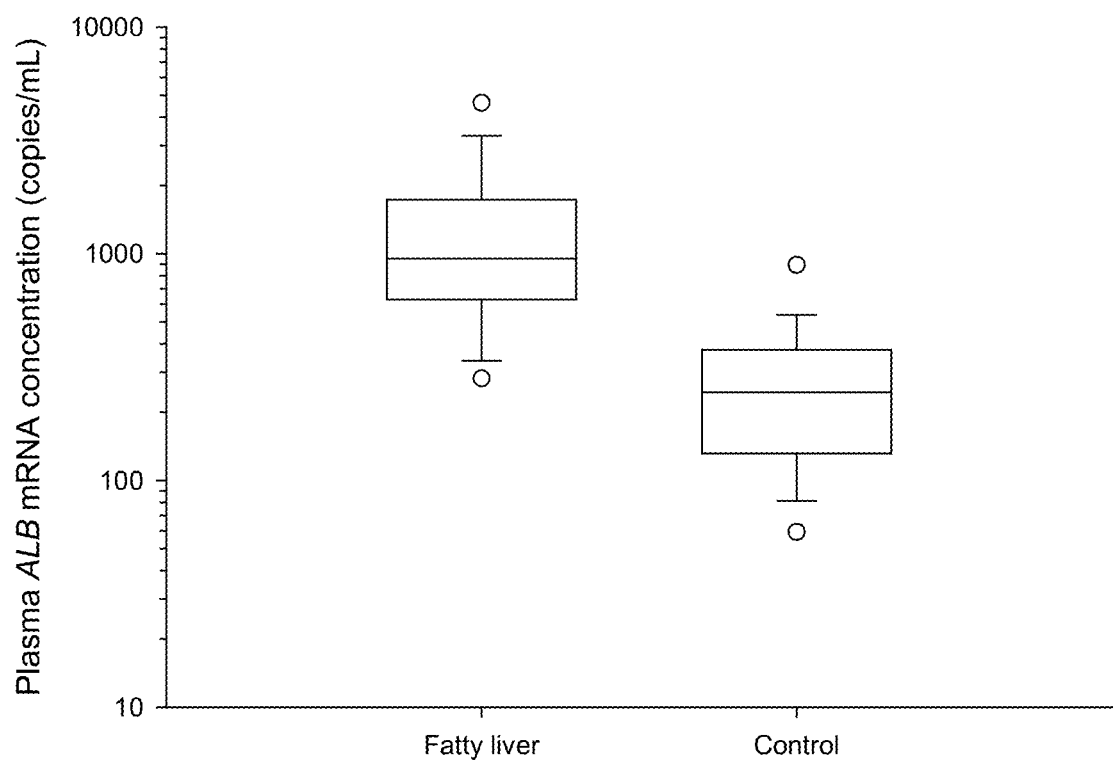
FIG. 13. Plasma ALB mRNA concentrations in cases with fatty liver disease and healthy controls. The upper and lower limits of the boxes and the lines across the boxes indicate the $75^{th}$ and $25^{th}$ percentiles and the median, respectively. The whisker caps indicate the $90^{th}$ and $10^{th}$ percentiles. Outliers are illustrated as open circles.
Figure 14:
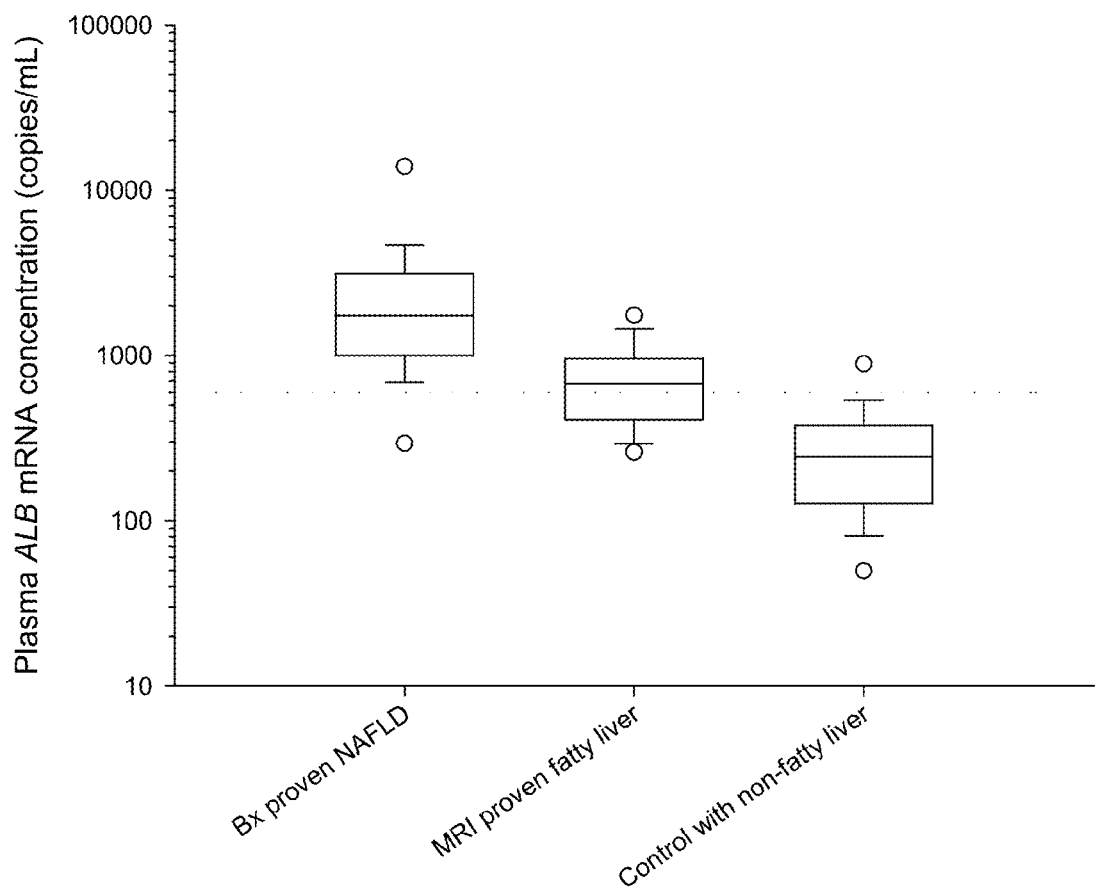
FIG. 14. Plasma ALB mRNA concentrations in cases with fatty liver disease diagnosed by liver biopsy (Bx), or diagnosed by magnetic resonance spectroscopy imaging (MRI) and healthy controls. The upper and lower limits of the boxes and the lines across the boxes indicate the $75^{th}$ and $25^{th}$ percentiles and the median, respectively. The whisker caps indicate the $90^{th}$ and $10^{th}$ percentiles. Outliers are illustrated as open circles. NAFLD, nonalcoholic fatty liver disease.
Figure 15:
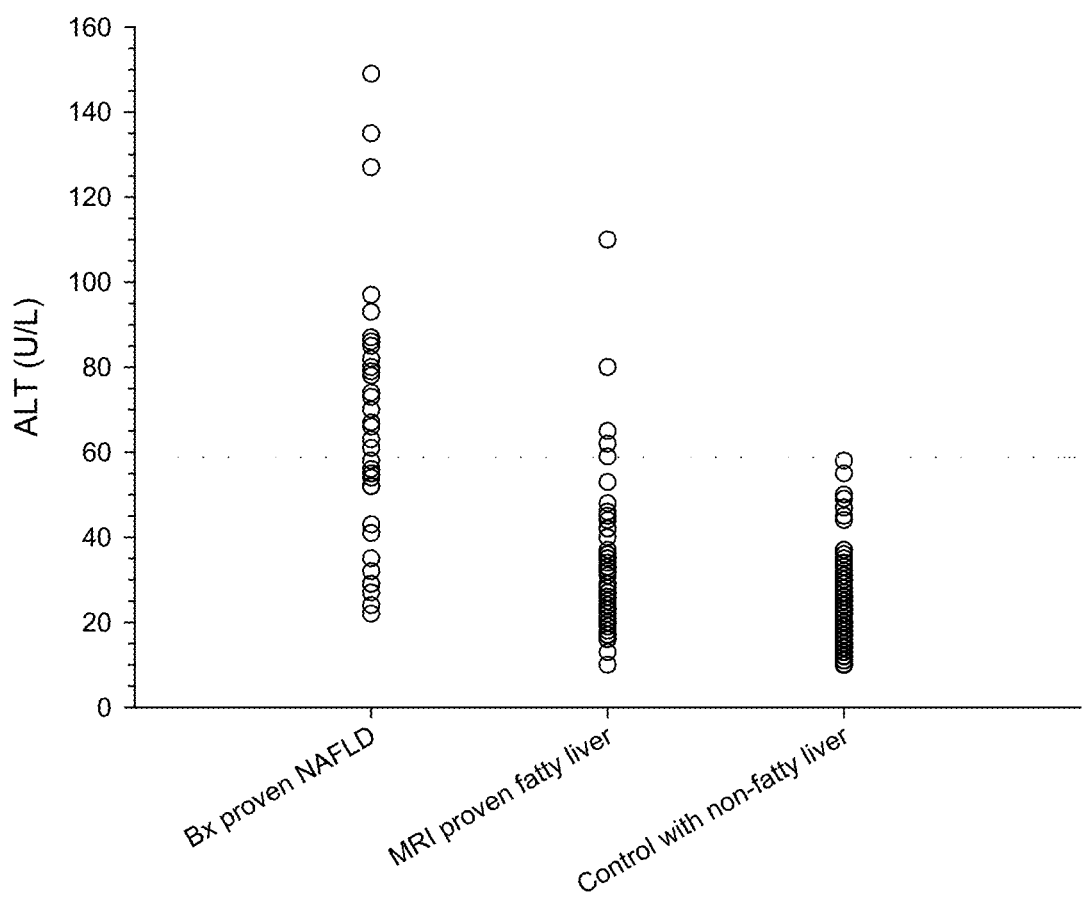
FIG. 15. Plasma ALT activity-concentrations in the subjects shown in FIG. 14. The dashed line indicates the reference cutoff value. Bx, biopsy; MRI, magnetic resonance spectroscopy imaging. NAFLD, nonalcoholic fatty liver disease.

The plasma ALB mRNA concentrations were statistically significantly higher among cases with fatty liver disease when compared with the controls (Mann-Whitney P<0.001) (FIG. 13). The comparisons were also statistically significant if the fatty liver disease cases were subdivided into those diagnosed by MRS or liver biopsy (Kruskal-Wallis followed by pairwise comparisons, P<0.0001 for all pairwise comparisons between the three groups) (FIG. 14). Plasma ALT was measured for these patients and it was not elevated in the majority of the cases (FIG. 15). Even in the group diagnosed with fatty liver disease by liver biopsy, 46% (16/35) had ALT activity-concentration within the reference cutoff.

III. Discussion

Fatty liver disease is considered an early stage of liver pathology which may progress to liver fibrosis, liver cirrhosis and even HCC. The elevation in plasma ALB mRNA in fatty liver disease patients when compared with controls indicates that plasma ALB mRNA is indeed a marker sensitive enough for the detection of early stage liver pathologies, such as fatty liver disease.

The group diagnosed with fatty liver disease by liver biopsy generally has more advanced stage fatty liver disease than those diagnosed by MRS. This is because individuals in the liver biopsy group either have symptoms or abnormal biochemical liver function test parameters to warrant the referral for the liver biopsy, whereas the MRS group comprised of asymptomatic volunteers. The data showed that the group diagnosed by liver biopsy had statistically significantly higher plasma ALB mRNA concentrations than the fatty liver disease cases diagnosed by MRS. This observation indicated that plasma ALB mRNA concentration correlates with severity of the liver pathology and can therefore be a tool for assessment of the stage of disease, for prognostication and for treatment monitoring. These data further showed that ALT is a less sensitive marker than plasma ALB mRNA for the detection of fatty liver disease and other early stage liver pathologies.

Based on the data obtained for all the presented examples, it has been consistently shown that plasma ALB mRNA is a sensitive marker of liver pathologies involving hepatocyte damage, death or apoptosis. The concentration of ALB mRNA in plasma becomes elevated when compared to that of healthy controls for liver pathologies involving hepatocyte damage, death or apoptosis. Such liver or hepatobiliary pathologies include acute conditions, for example acute hepatitis, including those due to toxic or viral causes, hypoxic damage, cholangitis and acute biliary tree obstruction. Such liver or hepatobiliary pathologies also include chronic conditions, for example, chronic hepatitis, including due to hepatitis B or hepatitis C viruses, fatty liver disease, liver fibrosis, liver cirrhosis, hepatocellular carcinoma but not including those that recurred after liver transplantation.

The present inventors' data showed that the magnitude of elevation in plasma ALB mRNA compared with healthy controls correlates with severity of the liver pathologies because it is likely to be reflecting the degree of liver cell damage, death or apoptosis. Thus, the plasma ALB mRNA concentration can be used to prognosticate and monitor the effectiveness of treatment for all the liver pathologies listed above.

Similarly, elevation in plasma ALB mRNA is shown to be sensitive enough to detect early stage liver diseases, such as fatty liver disease. All the liver pathologies involve hepatocyte damage, death or apoptosis. Therefore, elevated plasma ALB mRNA is also useful as a sensitive marker for the early stage detection of liver pathologies, for example, progression to active hepatitis in carrier of hepatitis B virus, decompensation or progression of liver cirrhosis, early stage hepatocellular carcinoma but not including those that recurred after liver transplantation.

All patents, patent applications, and other publications, including GenBank Accession Numbers, cited in this application are incorporated by reference in the entirety for all purposes.

TABLE 1

ALB genotypes of the informative transplantation recipients and donors

| Transplant type | Case No. | Original genotype of recipient | Genotype of donor | Post-transplant genotype in plasma of recipient | Post-transplant genotype in whole blood of recipient |
|---|---|---|---|---|---|
| LT | L1 | A | AG | AG | A |
| LT | L4 | A | AG | AG | A |
| LT | L6 | G | AG | AG | G |
| LT | L8 | AG | A | A | AG |
| LT | L9 | AG | A | A | — |
| LT | L11 | A | AG | AG | AG |
| LT | L12 | A | AG | AG | AG |
| LT | L18 | AG | A | A | AG |
| LT | L20 | A | G | G | G |
| LT | L22 | G | A | A | — |
| LT | L23 | AG | A | A | AG |
| LT | L24 | AG | A | A | AG |
| LT | L25 | AG | — | G | AG |
| LT | L27 | G | A | A | AG |
| LT | L29 | G | AG | AG | — |
| BMT | B1 | AG | A | AG | AG |
| BMT | B8 | A | AG | A | AG |
| BMT | B9 | AG | A | AG | — |
| BMT | B10 | AG | G | AG | G |
| BMT | B13 | AG | G | AG | AG |

LT, liver transplantation; BMT, bone marrow transplantation; —, not available.
The donor genotype for case L25 was not known as the patient underwent the liver transplantation in Mainland China.

TABLE 2

Profile of the study participants

| Group | HCC | Cirrhosis | Active CHB (HBV DNA ≥10,000 copies/mL) | Inactive CHB (HBV DNA <10,000 copies/mL) | Control |
|---|---|---|---|---|---|
| n | 35 | 25 | 24 | 23 | 207 |
| Sex | | | | | |
| M (%) | 33 (94%) | 19 (76%) | 20 (83%) | 17 (74%) | 141 (68%) |
| F (%) | 2 (6%) | 6 (24%) | 4 (17%) | 6 (26%) | 66 (32%) |
| Age (years) | 55 ± 10 | 61 ± 9 | 43 ± 12 | 47 ± 11 | 45 ± 10 |
| Albumin (g/L) | 42 (23-48) | 39 (26-47) | 44 (39-50) | 48 (42-49) | 46 (40-52) |
| Bilirubin (μmol/L) | 12 (6-50) | 24 (3-188) | 12 (4-34) | 13 (5-25) | 13 (2-29) |
| ALP (IU/L) | 86 (43-147) | 83 (47-210) | 70 (37-111) | 68 (40-101) | 65 (32-114) |
| ALT (IU/L) | 41 (21-317) | 40 (14-197) | 37 (12-73) | 25 (10-64) | 21 (10-58) |
| Hepatitis B surface antigen | | | | | |
| Positive | 29 | 18 | 24 | 23 | 0 |
| Negative | 3 | 1 | 0 | 0 | 207 |

TABLE 2-continued

Profile of the study participants

| Group | HCC | Cirrhosis | Active CHB (HBV DNA ≥10,000 copies/mL) | Inactive CHB (HBV DNA <10,000 copies/mL) | Control |
|---|---|---|---|---|---|
| Not known | 3 | 4 | 0 | 0 | 0 |
| Plasma ALB mRNA concentration (copies/mL) | 3 454 (136-57 047) | 2 486 (0-42 557) | 3 595 (156-1 500 000) | 1 642 (110-7 847) | 222 (0-2 279) |

HCC, hepatocellular carcinoma; CHB, chronic hepatitis B. Age is presented in mean ± SD. Levels of albumin, bilirubin, alkaline phosphatase (ALP), alanine transaminase (ALT) and plasma ALB mRNA concentration are presented in median (range).

TABLE 3

Primer and probe sequences for ALB SNP genotyping.

| Primers and probe | Sequences | SEQ ID NO: |
|---|---|---|
| Gene-specific primer for reverse transcription | 5'-TCTTTTGTTGCCTTGGGCTTGT-3' | 1 |
| RNA forward PCR primer | 5'-ACGTTGGATGCTGAGAAGGAGAGACAAATCAAGAA-3' | 2 |
| RNA reverse PCR primer | 5'-ACGTTGGATGCTTTTGTTGCCTTGGGCTTG-3' | 3 |
| DNA forward PCR primer | 5'-ACGTTGGATGTTTCCATTCAAACTCAGTGCACT-3' | 4 |
| DNA reverse PCR primer | 5'-ACGTTGGATGTGCTCTTTTGTTGCCTTGGG-3' | 5 |
| hME extension primer | 5'-TTGGGCTTGTGTTTCAC-3' | 6 |

NB. All PCR primers for SNP genotyping were designed with an addition of a 10-base tag (bold) to avoid interference in mass spectra.

TABLE 4

Sequences of primers, probe and calibration standard for ALB mRNA quantification.

| Primers, probe and synthetic DNA oligonucleotides | Sequences | SEQ ID NO: |
|---|---|---|
| ALB forward primer | 5'-TCTCTTTAGCTCGGCTTATTCC-3' | 7 |
| ALB reverse primer | 5'-TCTTTAAACCGATGAGCAACCT-3' | 8 |
| ALB Probe | 5'-(FAM)CGAGATGCACACAAGAG(MGBNFQ)-3' | 9 |
| ALB calibration standard | 5'-TTTTCTCTTTAGCTCGGCTTATTCCAGGGGTGTGTTTCGTCGA GATGCACACAAGAGTGAGGTTGCTCATCGGTTTAAAGATTT-3' | 10 |

NB. FAM is 6-carboxyfluorescein, MGB is minor groove binder and NFQ is non-fluorescent quencher dye.

TABLE 5

Profile of participants with plasma ALT <58 IU/L

| Group | HCC | Cirrhosis | Active CHB (HBV DNA ≥10,000 copies/mL) | Inactive CHB (HBV DNA <10,000 copies/mL) | Control |
|---|---|---|---|---|---|
| N | 24 | 18 | 20 | 22 | 207 |
| Ratio of participants with normal ALT to all participants (%) | 24/35 (69%) | 18/25 (72%) | 20/24 (83%) | 22/23 (96%) | 207/207 (100%) |
| Sex | | | | | |
| M (%) | 22 (92%) | 14 (78%) | 16 (80%) | 16 (73%) | 141 (68%) |
| F (%) | 2 (8%) | 4 (22%) | 4 (28%) | 6 (27%) | 66 (32%) |
| Age (years) | 55 ± 11 | 58 ± 9 | 44 ± 12 | 43 ± 12 | 45 ± 10 |

TABLE 5-continued

Profile of participants with plasma ALT <58 IU/L

| Group | HCC | Cirrhosis | Active CHB (HBV DNA ≥10,000 copies/mL) | Inactive CHB (HBV DNA <10,000 copies/mL) | Control |
|---|---|---|---|---|---|
| Albumin (g/L) | 43 | 39 | 44 | 45 | 46 |
|  | (24-48) | (26-47) | (40-50) | (42-49) | (40-52) |
| Bilirubin (mmol/L) | 12 | 23 | 12 | 11 | 13 |
|  | (6-50) | (3-188) | (4-20) | (5-25) | (2-29) |
| ALP (IU/L) | 86 | 82 | 71 | 63 | 65 |
|  | (43-143) | (47-136) | (40-111) | (40-101) | (32-114) |
| ALT (IU/L) | 41 | 32 | 35 | 27 | 21 |
|  | (21-317) | (14-58) | (12-56) | (10-53) | (10-58) |
| Hepatitis B surface antigen |  |  |  |  |  |
| Positive | 21 | 14 | 20 | 22 | 0 |
| Negative | 2 | 1 | 0 | 0 | 207 |
| Not known | 1 | 3 | 0 | 0 | 0 |
| Plasma ALB mRNA concentration (copies/mL) | 3 638 (136-42 675) | 2 167 (0-23 354) | 2 734 (156-90 693) | 1 326 (110-5 542) | 222 (0-2 279) |

HCC, hepatocellular carcinoma; CHB, chronic hepatitis B. Age is presented in mean ± SD. Levels of albumin, bilirubin, alkaline phosphatase (ALP), alanine transaminase (ALT) and plasma ALB mRNA concentration are presented in median (range).

TABLE 6

| Patient No. | Plasma ALB mRNA (copies/mL of plasma) at recruitment | ALT level (U/L) at recruitment | Subsequent consequence | No. weeks from recruitment to the time with first adverse outcome developed |
|---|---|---|---|---|
| 1 | 0 | 23 | Well | NA |
| 2 | 320 | 28 | Well | NA |
| 3 | 430 | 69 | Cholangitis; Hepatic duct strictures | 111 |
| 4 | 218 | 36 | Well | NA |
| 5 | 6,696 | 53 | Mild graft rejection followed with prominent IHD stones and repeated cholangitis | 97 |
| 7 | 719 | 32 | Well | NA |
| 8 | 25,769 | 53 | Chronic graft rejection confirmed by liver biopsy | 60 |
| 9 | 1,657 | 125 | Emergency admission with Jaundice; died of septic shock secondary to spontaneous bacterial peritonitis | 91 |
| 11 | 350 | 35 | Well | NA |
| 12 | 1,209 | 50 | Chronic graft rejection with new onset of alcoholic cirrhosis and portal hypertension | 124 |
| 13 | 376 | 83 | Well | NA |
| 14 | 918 | 32 | Well | NA |
| 15 | 1,578 | 26 | 9 weeks after blood sampling, admitted for anastomotic stenosis with cholangitis. 20 weeks after blood sampling, died of hepatocellular carcinoma with bone metastasis | 9 |
| 17 | 1,635 | 48 | Bile duct stones and died of sepsis and ischaemic heart disease | 58 |
| 18 | 632 | 43 | Well | NA |
| 19 | 0 | 59 | Well | NA |
| 20 | 1,732 | 69 | Mild fatty liver confirmed by ultrasound; otherwise well | NA |
| 21 | 37 | 26 | Well | NA |
| 23 | 100 | 33 | Well | NA |
| 24 | 107 | 31 | Obstructive jaundice | 66 |
| 25 | 170 | 28 | Well | NA |
| 27 | 55 | 25 | Well | NA |
| 28 | 365 | 26 | Well | NA |
| 29 | 826 | 10 | Well | NA |

Plasma ALB mRNA concentrations greater than 835 copies/mL; elevated ALT activity concentration (>58 IU/L); and adverse clinical consequence are shown in bold font.

TABLE 7

Table listing the liver-associated complications developed by the post-liver transplantation recipients in the Unstable group during the study period

| Case No. | Complications | Time of diagnosis (Week No. from the time of enrollment) |
|---|---|---|
| U01 | Cholangitis with hepatic junction stenosis | 50 |
| | Cholestasis | 69 |
| U02 | Cholesterolosis with drug-induced like hepatic injury | 66 |
| U03 | Cholangitis | 25 |
| U04 | Post-transplant lymphoproliferative disease | 63 |
| | Severe portal gastropathy with gastritis and cholangitis | 111 |
| U05 | Mild rejection with cholangitis | 97 |
| | Cholangitis with Escherichia coli infection | 108 |
| U06 | Budd-chiari syndrome | 96 |
| U07 | Recurrence of alcoholic cirrhosis with mild chronic rejection | 0 |
| U08 | Chronic rejection | 60 |
| U09 | HCV cirrhosis with hepatomegaly | 116 |
| U10 | Liver abscess | 74 |
| | Liver fibrosis | 107 |

What is claimed is:

1. A method for monitoring a post-liver transplant patient, comprising the steps of:
    (a) determining the concentration of albumin mRNA in an acellular blood sample taken from the patient, wherein the determining comprises amplification of the albumin mRNA by a polymerase chain reaction (PCR), and wherein a primer comprising the polynucleotide sequence set forth in SEQ ID NO:7 or 8 is used in the PCR;
    (b) comparing the concentration of albumin mRNA from step (a) with a standard control; and
    (c) detecting an increased risk of post-transplant liver complication in the patient when the concentration obtained in step (b) is greater than the standard control, and detecting no increased risk of post-transplant liver complication in the patient when the concentration obtained in step (b) is no greater than the standard control, wherein the post-transplant liver complication is not recurring hepatocellular carcinoma (HCC).

2. The method of claim 1, wherein the patient has normal alanine aminotransferase (ALT) test results.

3. The method of claim 1, wherein the post-transplant liver complication is cirrhosis or rejection.

4. The method of claim 1, wherein the blood sample is plasma.

5. The method of claim 1, wherein the blood sample is serum.

6. The method of claim 1, wherein the PCR is a reverse transcriptase (RT)-PCR.

7. The method of claim 1, wherein the PCR is digital PCR.

8. The method of claim 1, wherein the PCR is real-time quantitative PCR.

9. The method of claim 1, wherein step (a) comprises mass spectrometry or hybridization to a microarray, fluorescence probe, or molecular beacon.

10. The method of claim 1, further comprising repeating steps (a) to (c) at a later time.

11. The method of claim 10, wherein steps (a) to (c) are repeated multiple times.

12. The method of claim 1, wherein determining the concentration of albumin mRNA comprises a one-step assay.

13. The method of claim 12, wherein the one-step assay comprises amplifying a 5' region of the albumin mRNA.

14. The method of claim 1, wherein the patient has shown no symptoms of liver abnormality after receiving the liver transplant.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: synthetic albumin (ALB) gene-specific primer
      for reverse transcription in SNP genotyping

<400> SEQUENCE: 1
tcttttgttg ccttgggctt gt                                        22

<210> SEQ ID NO 2
<211> LENGTH: 35
<212> TYPE: DNA
<213> ORGANISM: Artificial Sequence
<220> FEATURE:
<223> OTHER INFORMATION: synthetic RNA forward PCR primer for albumin
      (ALB) SNP genotyping

<400> SEQUENCE: 2
acgttggatg ctgagaagga gagacaaatc aagaa                          35

<210> SEQ ID NO 3
<211> LENGTH: 30
<212> TYPE: DNA
<213> ORGANISM: Artificial Sequence
<220> FEATURE:
<223> OTHER INFORMATION: synthetic RNA reverse PCR primer for albumin
      (ALB) SNP genotyping

<400> SEQUENCE: 3
acgttggatg cttttgttgc cttgggcttg                                30

<210> SEQ ID NO 4
<211> LENGTH: 33
<212> TYPE: DNA
<213> ORGANISM: Artificial Sequence
<220> FEATURE:
<223> OTHER INFORMATION: synthetic DNA forward PCR primer for albumin
      (ALB) SNP genotyping

<400> SEQUENCE: 4
acgttggatg tttccattca aactcagtgc act                            33

```
<210> SEQ ID NO 5
<211> LENGTH: 30
<212> TYPE: DNA
<213> ORGANISM: Artificial Sequence
<220> FEATURE:
<223> OTHER INFORMATION: synthetic DNA reverse PCR primer for albumin
      (ALB) SNP genotyping

<400> SEQUENCE: 5
acgttggatg tgctcttttg ttgccttggg                                        30

<210> SEQ ID NO 6
<211> LENGTH: 17
<212> TYPE: DNA
<213> ORGANISM: Artificial Sequence
<220> FEATURE:
<223> OTHER INFORMATION: synthetic homogeneous MassEXTEND (hME) assay
      extension primer for albumin (ALB) SNP genotyping

<400> SEQUENCE: 6
ttgggcttgt gtttcac                                                      17

<210> SEQ ID NO 7
<211> LENGTH: 22
<212> TYPE: DNA
<213> ORGANISM: Artificial Sequence
<220> FEATURE:
<223> OTHER INFORMATION: synthetic albumin (ALB) forward primer for mRNA
      quantification

<400> SEQUENCE: 7
tctctttagc tcggcttatt cc                                                22

<210> SEQ ID NO 8
<211> LENGTH: 22
<212> TYPE: DNA
<213> ORGANISM: Artificial Sequence
<220> FEATURE:
<223> OTHER INFORMATION: synthetic albumin (ALB) reverse primer for mRNA
      quantification

<400> SEQUENCE: 8
tctttaaacc gatgagcaac ct                                                22

<210> SEQ ID NO 9
<211> LENGTH: 17
<212> TYPE: DNA
<213> ORGANISM: Artificial Sequence
<220> FEATURE:
<223> OTHER INFORMATION: synthetic albumin (ALB) probe for mRNA
      quantification
<220> FEATURE:
<221> NAME/KEY: modified_base
<222> LOCATION: (1)...(1)
<223> OTHER INFORMATION: c modified by 6-carboxyfluorescein (FAM)
<220> FEATURE:
<221> NAME/KEY: modified_base
<222> LOCATION: (17)...(17)
<223> OTHER INFORMATION: g modified by minor groove binder (MGB) and
      non-fluorescent quencher dye (NFQ)

<400> SEQUENCE: 9
cgagatgcac acaagag                                                      17

<210> SEQ ID NO 10
<211> LENGTH: 84
<212> TYPE: DNA
<213> ORGANISM: Artificial Sequence
<220> FEATURE:
```

```
<223> OTHER INFORMATION: synthetic albumin (ALB) calibration standard
      for mRNA quantification

<400> SEQUENCE: 10
ttttctcttt agctcggctt attccagggg tgtgtttcgt cgagatgcac acaagagtga      60
ggttgctcat cggtttaaag attt                                             84
```